(12) United States Patent
Borgmeier et al.

(10) Patent No.: US 7,091,377 B2
(45) Date of Patent: *Aug. 15, 2006

(54) MULTIMETAL OXIDE MATERIALS

(75) Inventors: Frieder Borgmeier, Mannheim (DE); Martin Dieterle, Mannheim (DE); Hartmut Hibst, Schriesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 103 days.

This patent is subject to a terminal disclaimer.

(21) Appl. No.: 10/684,559

(22) Filed: Oct. 15, 2003

(65) Prior Publication Data

US 2004/0082190 A1    Apr. 29, 2004

(30) Foreign Application Priority Data

| Oct. 17, 2002 | (DE) | ............................... 102 48 584 |
| Nov. 20, 2002 | (DE) | ............................... 102 54 278 |
| Nov. 20, 2002 | (DE) | ............................... 102 54 279 |

(51) Int. Cl.
B01J 29/06    (2006.01)

(52) U.S. Cl. .................. 562/598; 562/549; 562/542; 562/311; 562/312; 562/545; 562/600; 502/305; 502/306; 502/307; 502/308; 502/310; 502/311; 502/312; 502/313; 502/315; 502/317; 502/318; 502/309; 502/321; 502/325; 502/340; 502/344; 502/353; 502/304

(58) Field of Classification Search ................ 502/305, 502/306, 307, 308, 310, 311, 312, 313, 315, 502/317, 318, 309, 321, 325, 340, 344, 353, 502/304

See application file for complete search history.

(56) References Cited

U.S. PATENT DOCUMENTS

| 6,036,880 | A | | 3/2000 | Komada et al. | |
|---|---|---|---|---|---|
| 6,043,185 | A | * | 3/2000 | Cirjak et al. ................ | 502/311 |
| 6,063,728 | A | | 5/2000 | Hinago et al. | |
| 6,143,916 | A | | 11/2000 | Hinago et al. | |
| 6,383,978 | B1 | * | 5/2002 | Bogan, Jr. .................. | 502/311 |
| 6,403,525 | B1 | * | 6/2002 | Chaturvedi et al. ......... | 502/311 |
| 6,407,031 | B1 | * | 6/2002 | Chaturvedi et al. ......... | 502/311 |
| 6,407,280 | B1 | * | 6/2002 | Chaturvedi et al. ......... | 558/319 |
| 6,589,907 | B1 | * | 7/2003 | Chaturvedi et al. ......... | 502/311 |
| 6,610,629 | B1 | * | 8/2003 | Hinago et al. ............... | 502/300 |
| 6,642,173 | B1 | * | 11/2003 | Bogan, Jr. .................. | 502/311 |
| 6,734,136 | B1 | * | 5/2004 | Chaturvedi et al. ......... | 502/215 |
| 2003/0187298 | A1 | * | 10/2003 | Borgmeier et al. ......... | 562/546 |
| 2004/0097368 | A1 | * | 5/2004 | Borgmeier et al. ......... | 502/312 |

FOREIGN PATENT DOCUMENTS

| DE | 198 35 247 | 2/1999 |
|---|---|---|
| DE | 101 18 814 | 10/2002 |
| EP | 0 318 295 | 5/1989 |
| EP | 0 512 846 | 11/1992 |
| EP | 0 529 853 | 3/1993 |
| EP | 0 603 836 | 6/1994 |
| EP | 0 608 838 | 8/1994 |
| EP | 0 767 164 | 4/1997 |
| EP | 0 895 809 | 2/1999 |
| EP | 0 962 253 | 12/1999 |
| EP | 1 192 982 | 4/2002 |
| EP | 1 192 983 | 4/2002 |
| EP | 1 192 986 | 4/2002 |
| EP | 1 192 987 | 4/2002 |
| EP | 1 254 707 | 11/2002 |
| EP | 1 254 709 | 11/2002 |
| EP | 1 254 710 | 11/2002 |
| JP | 7-232071 | 9/1995 |
| JP | 8-57319 | 3/1996 |
| JP | 11-169719 | 6/1999 |
| WO | WO 00/29105 | 5/2000 |
| WO | WO 00/29106 | 5/2000 |
| WO | WO 00/38833 | 7/2000 |
| WO | WO 00/69802 | 11/2000 |
| WO | WO 02/06199 | 1/2002 |
| WO | WO 02/051539 | 7/2002 |
| WO | WO 02/083615 | 10/2002 |

OTHER PUBLICATIONS

H. Watanabe, et al., Applied Catalysis A: General, Elsevier Science, vol. 194-195, XP-004272252, pp. 479-485, "New Synthesis Route for Mo—V—Nb—Te Mixed Oxides Catalyst for Propane Ammoxidation", Mar. 2000.

T. Ushikubo, et al., Spillover and Migration of Surface Species on Catalysts, pp. 473-480, "Ammoxidation of Propane Over Mo—V—Nb—Te Mixed Oxide Catalysts", 1997.

Patent Abstracts of Japan, JP 11-169716, Jun. 29, 1999.

* cited by examiner

Primary Examiner—Christina Johnson
(74) Attorney, Agent, or Firm—Oblon, Spivak, McClelland, Maier & Neustadt, P.C.

(57) ABSTRACT

A multimetal oxide material contains the elements Mo, V and Te and/or Sb and at least one of the elements Nb, Ti, W, Ta and Ce and promoters and has a specific X-ray diffraction pattern. Moreover, such a multimetal oxide material is used as a catalyst for heterogeneously catalyzed gas-phase partial oxidations of hydrocarbons.

33 Claims, 17 Drawing Sheets

MULTIMETAL OXIDE MATERIALS

FIELD OF THE INVENTION

The present invention relates to multimetal oxide materials of the stoichiometry I $$Mo_1V_aM^1_bM^2_cM^3_dO_n \qquad (I),$$

where
M[1] is at least one of the elements from the group consisting of Te and Sb;
M[2] is at least one of the elements from the group consisting of Nb, Ti, W, Ta and Ce;
M[3] is at least one of the elements from the group consisting of Pb, Ni, Co, Bi, Pd, Ag, Pt, Cu, Au, Ga, Zn, Sn, In, Re, Ir, Sm, Sc, Y, Pr, Nd and Tb;
a is from 0.01 to 1,
b is from >0 to 1;
c is from >0 to 1;
d is from >0 to 0.5 and
n is a number which is determined by the valency and frequency of the elements other than oxygen in (I),
whose X-ray diffraction pattern has reflections h, i and k whose peaks are at the diffraction angles 2θ 22.2±0.50° (h), 27.3±0.5° (i) and 28.2±0.5° (k),
the reflection h being the one with the strongest intensity within the X-ray diffraction pattern and having an FWHH of not more than 0.5°,
the intensity $P_i$ of the reflection i and the intensity $P_k$ of fulfilling the relationship 0.65≦R≦0.85, where R is the intensity ratio defined by the formula $$R = P_i/(P_i + P_k)$$

and
the FWHH of the reflection i and of the reflection k being in each case 1°,
wherein the at least one multimetal oxide material (I) is one whose X-ray diffraction pattern has no reflection with the peak position 2θ=50.0±0.3°.

The present invention furthermore relates to the preparation of multimetal oxide materials (I) and their use with the heterogeneously catalyzed partial oxidation and/or ammoxidation of saturated and/or unsaturated hydrocarbons.

DESCRIPTION OF THE RELATED ART

Multimetal oxide materials of the stoichiometry (I) and having a stoichiometric coefficient d=0, which are obtainable by calcining a thorough dry mixture of their elemental constituents in an oxygen-containing atmosphere, are disclosed, for example, in EP-A 318295. They are suitable, for example, for the heterogeneously catalyzed ammoxidation of propane or isobutane for the preparation of acrylonitrile or methacrylonitrile and have a high amorphous structural fraction.

EP-A 512846 discloses that the performance of multimetal oxide materials of EP-A 318295 can be improved by adding promoter elements M[3] when they are intended to be used as catalysts for the partial ammoxidation of saturated hydrocarbons.

EP-A 529853, EP-A 603836, EP-A 608838, EP-A 767164, EP-A 895809 and EP-A 962253 disclose multimetal oxide materials of the stoichiometry (I) and having a stoichiometric coefficient d=0, which are obtainable by calcining a thorough dry mixture of their elemental constituents in an atmosphere substantially free of oxygen. They are even more suitable than the multimetal oxide materials of EP-A 318295 and of EP-A 512846 as catalysts for the heterogeneously catalyzed partial ammoxidation and/or oxidation of saturated hydrocarbons, the latter in particular when the thorough dry mixture was produced as a catalyst precursor by spray drying.

In the publications cited, this is attributable to the fact that, as a result of their preparation, these multimetal oxide materials are substantially present in crystalline form having a specific crystal structure, wherein their X-ray diffraction pattern has reflections with a strong intensity at the 2θ peak positions 22.1±0.3°, 28.2±0.3°, 36.2±0.3°, 45.2±0.3° and 50.0+0.3°.

DE-A 19835247, EP-A 1090684 and WO 0206199 disclose that the abovementioned specific crystal structure forms only one crystalline phase in which such multimetal oxide materials can occur. This crystalline phase is referred to in the abovementioned literature as a rule as the k phase.

A second specific crystal structure in which the relevant multimetal oxide materials can occur is referred to as a rule as the i phase. Typical of its X-ray diffraction content, according to the abovementioned publications, is, inter alia, that it has reflections of the strongest intensity at the 2⊖ peak positions 22.2±0.4°, 27.3±0.4° and 28.2±0.4°, in contrast to the k phase in which, however, there is no reflection at the 2⊖ peak position 50.0±0.3°.

For example, according to EP-A 529853, EP-A 608838 and EP-A 603836, the k phase is responsible for the catalytic activity of multimetal oxide materials mentioned there.

The method of preparation as described above usually gives neither pure k phase nor pure i phase but a crystalline solid solution which comprises an intergrown mixture of k and i phases.

In EP-A 1192987, EP-A 1192986, EP-A 1192983 and EP-A 1192982, such multimetal oxide materials in the form of solid solutions are prepared and it is shown that their performance can be improved by adding promoter elements M[3] when it is intended to use them as catalysts for partial ammoxidation and/or oxidation of saturated hydrocarbons, the k phase being attributed to the decisive role.

In contrast, JP-A 11-169716 considers that both the k phase and the i phase play a decisive role in the catalytic activity of such multimetal oxide materials in the form of solid solutions in the partial ammoxidation of saturated hydrocarbons. According to this publication, the k phase is responsible for a satisfactory selectivity of nitrile formation and the i phase for a sufficient conversion of the saturated hydrocarbon.

In Ammoxidation of propane over Mo—V—Nb—Te mixed oxide catalysts from Spillover and Migration of Surface on Catalysts, Ed. by Can Li and Quin Xin, Elsevier Science B. V. (1997), page 473 et seq., the inventors of JP-A 11-169716 emphasize this concept, which is also supported by DE-A 19835247 and EP-A 895089.

In comparison, JP-A 7-232071 and WO 0206199 disclose that multimetal oxide materials present exclusively in the i-phase structure are also suitable as catalysts for the heterogeneously catalyzed partial ammoxidation and/or oxidation of saturated hydrocarbons.

Furthermore, experiments have already been carried out in which it is shown that multimetal oxide materials present exclusively in the k-phase structure are catalytically inactive and which support the concept of JP-A 11-169716 whereby the i phase is responsible for the activity and the k phase is responsible only for maximizing the selectivity.

WO 00/29106, WO 00/29105, WO 00/38833 and WO 00/69802 disclose multimetal oxide materials which contain promoters and have a substantially amorphous structure represented by very broad reflections in the X-ray diffraction pattern and which are likewise recommended as catalysts for partial oxidations.

DE-A 10118814 and PCT/EP/02/04073 disclose that multimetal oxide materials comprising pure i phase are also suitable catalysts for partial oxidations of unsaturated hydrocarbons.

JP-A 8-57319 discloses that Mo- and/or V-containing multimetal oxide active materials can be activated by treatment with acid.

What is disadvantageous about the stated prior art, however, is that, on the one hand, it does not answer the question as to whether the promoters are incorporated both into the i phase and into the k phase and whether they influence the catalytic activity of both phases and, on the other hand, their multimetal oxide materials are not completely satisfactory, with regard to the selectivity of the formation of desired product, as catalysts for the heterogeneously catalyzed partial oxidation and/or ammoxidation of saturated and/or unsaturated hydrocarbons.

SUMMARY OF THE INVENTION

It is an object of the present invention to answer the unanswered question and to provide multimetal oxide materials which are improved in the context of the object.

We have found that this object is achieved by the multimetal oxide materials (I) defined at the outset (all data in this document which are based on an X-ray diffraction pattern relate to an X-ray diffraction pattern produced using Cu—Kα radiation as X-rays (Siemens diffractometer Theta-Theta D-5000, tube voltage: 40 kV, tube current: 40 mA, aperture V20 (variable), collimator V20 (variable), secondary monochromator (0.1 mm), detector aperture (0.6 mm), measuring interval (2Θ):0.02°, measuring time per step: 2.4 s, detector: scintillation counter); the definition of the intensity of a reflection in the X-ray diffraction pattern is based in this document on the definition stated in DE-A 19835247, DE-A 10122027, DE-A 10051419 and DE-A 10046672; the same applies to the definition of the full width at half height).

DETAILED DESCRIPTION OF AN EMBODIMENT OF THE INVENTION

Figure 1:
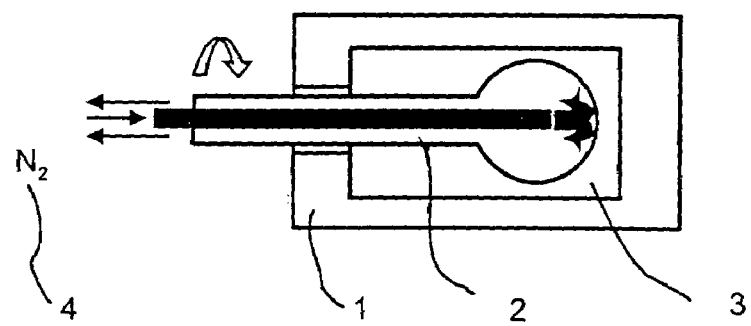
FIG. 1 shows a rotating-bulb furnace for heating a spray-dried powder.

According to the invention, preferably $0.67 \leq R \leq 0.75$, very particularly preferably R=0.69 to 0.75 or R=0.71 to 0.74 or R=0.72.

In addition to the reflections h, i and k, the X-ray diffraction pattern of novel multimetal oxide materials (I) contains, as a rule, further reflections whose peaks are at the following diffraction angles (2Θ):

9.0±0.4° (l),
6.7±0.4° (o) and
7.9±0.4° (p).

It is furthermore advantageous if the X-ray diffraction pattern additionally contains a reflection whose peak is at the diffraction angle (2Θ) of 45.2±0.4° (q).

Frequently, the X-ray diffraction pattern of multimetal oxide materials (I) also contains the reflections 29.2±0.4° (m) and 35.4±0.4° (n) (peak positions).

If the intensity 100 is assigned to the reflection h, it is advantageous, according to the invention, if the reflections i, l, m, n, o, p and q have, on the same intensity scale, the following intensities:

i: from 5 to 95, frequently from 5 to 80, in some cases from 10 to 60;
l: from 1 to 30;
m: from 1 to 40;
n: from 1 to 40
o: from 1 to 30;
p: from 1 to 30 and
q: from 5 to 60.

If the X-ray diffraction pattern of the novel multimetal oxide materials (I) contains reflections from the abovementioned additional reflections, the full width at half height thereof is as a rule ≦1°.

The specific surface area of novel multimetal oxide materials (I) is often from 1 to 40, frequently from 11 or 12 to 40, and often from 15 or 20 to 40 or 30, m²/g (determined by the BET method, nitrogen).

According to the invention, the stoichiometric coefficient a of the novel multimetal oxide materials (I), independently of the preferred ranges for the other stoichiometric coefficients of the multimetal oxide materials (I), is preferably from 0.05 to 0.6, particularly preferably from 0.1 to 0.6 or 0.5.

Independently of preferred ranges for the other stoichiometric coefficients of the multimetal oxide materials (I), the stoichiometric coefficient b is preferably from 0.01 to 1, particularly preferably from 0.01 or 0.1 to 0.5 or 0.4.

The stoichiometric coefficient c of the novel multimetal oxide materials (I), independently of the preferred ranges for the other stoichiometric coefficients of the multimetal oxide materials (I), is from 0.01 to 1, particularly preferably from 0.01 or 0.1 to 0.5 or 0.4. A very particularly preferred range for the stoichiometric coefficient c which, independently of the preferred ranges for the other stoichiometric coefficients of the novel multimetal oxide materials (I), can be combined with all other preferred ranges in this document, is from 0.05 to 0.2.

According to the invention, the stoichiometric coefficient d of the novel multimetal oxide materials (I), independently of the preferred ranges for the other stoichiometric coefficients of the multimetal oxide materials (I), is preferably from 0.00005 or 0.0005 to 0.5, particularly preferably from 0.001 to 0.5, frequently from 0.002 to 0.3, often from 0.005 or 0.01 to 0.1.

Novel multimetal oxide materials (I) whose stoichiometric coefficients a, b, c and d are simultaneously in the following ranges are particularly advantageous:
a=from 0.05 to 0.6;
b=from 0.01 to 1 (or from 0.01 to 0.5);
c=from 0.01 to 1 (or from 0.01 to 0.5) and
d=from 0.0005 to 0.5 (or from 0.001 to 0.3).

Novel multimetal oxide materials (I) whose stoichiometric coefficients a, b, c and d are simultaneously in the following ranges are very particularly advantageous:
a=from 0.1 to 0.6;
b=from 0.1 to 0.5;
c=from 0.1 to 0.5 and
d=from 0.001 to 0.5 or from 0.002 to 0.3 or from 0.005 to 0.1.

$M^1$ is preferably Te.

All of the abovementioned is especially applicable when at least 50, very particularly preferably at least 75 or 100, mol %, based on its total amount, of $M^2$ is Nb.

However, it is also especially applicable, independently of the meaning of $M^2$, when $M^3$ is at least one element from the group consisting of Ni, Co, Bi, Pd, Ag, Au, Pb and Ga or at least one element from the group consisting of Ni, Co, Pd and Bi.

However, all of the abovementioned is also especially applicable when at least 50 or at least 75 or at least 100 mol %, based on its total amount, of $M^2$ is Nb and $M^3$ is at least one element from the group consisting of Ni, Co, Bi, Pd, Ag, Au, Pb and Ga.

However, all of the abovementioned is also especially applicable when at least 50 or at least 75 or 100 mol %, based on its total amount, of $M^2$ is Nb and $M^3$ is at least one element from the group consisting of Ni, Co, Pd and Bi.

Very particularly preferably all statements regarding the stoichiometric coefficients are applicable when $M^1$ is Te, $M^2$ is Nb and $M^3$ is at least one element from the group consisting of Ni, Co and Pd.

Further stoichiometries suitable according to the invention are those which have been disclosed for the multimetal oxide materials of the stoichiometry (I) in the prior art cited at the outset.

The principle of a controlled process for the preparation of the novel multimetal oxide materials (I) is disclosed, for example, by WO 0206199 and the reference cited in this publication. According to these, a multimetal oxide material which has the stoichiometry (I) but is a generally intimately intergrown solid solution comprising i phase and other phases (e.g. k phase) is first prepared in a manner known per se. The i-phase fraction can then be isolated from the solid solution by washing out the other phases, for example the k phase, with suitable liquids. Suitable liquids of this type are, for example, aqueous solutions of organic acids (e.g. oxalic acid, formic acid, acetic acid, citric acid and tartaric acid), inorganic acids (e.g. nitric acid), alcohols and aqueous hydrogen peroxide solutions. Furthermore, JP-A 7-232071 also discloses a process for the preparation of multimetal oxide materials comprising i phase.

Solid solutions comprising i phase and k phase are obtained, as a rule, by the preparation process described in the prior art (cf. for example DE-A 19835247, EP-A 529853, EP-A 603836, EP-A 608838, EP-A 895809, DE-A 19835247, EP-A 962253, EP-A 1080784, EP-A 1090684, EP-A 1123738, EP-A 1192987, EP-A 1192986, EP-A 1192982, EP-A 1192983 and EP-A 1192988). According to these processes, a very thorough, preferably finely divided, dry mixture is produced from suitable sources of the elemental constituents of the multimetal oxide material and said mixture is treated thermally at from 350 to 700° C. or from 400 to 650° C. or from 400 to 600° C. The thermal treatment can be carried out in principle under either an oxidizing, a reducing or an inert atmosphere. A suitable oxidizing atmosphere is, for example, air, air enriched with molecular oxygen or air depleted in oxygen. However, the thermal treatment is preferably carried out under an inert atmosphere, for example under molecular nitrogen and/or noble gas. Usually, the thermal treatment is carried out at atmospheric pressure (1 atm). Of course, the thermal treatment can also be carried out under reduced or superatmospheric pressure.

If the thermal treatment is carried out under a gaseous atmosphere, this may be either stationary or flowing. It preferably flows. Altogether, the thermal treatment may take up to 24 hours or more.

The thermal treatment is preferably first carried out under an oxidizing (oxygen-containing) atmosphere (e.g. under air) at from 150 to 400° C. or from 250 to 350° C. (=preliminary decomposition step). Thereafter, the thermal treatment is expediently continued under inert gas at from 350 to 700° C. or from 400 to 650° C. or from 450 to 600° C. Of course, the thermal treatment can also be carried out in such a way that, before its thermal treatment, the catalyst precursor material is first pelleted (if necessary after pulverization and, if required, with the addition of from 0.5 to 2% by weight of finely divided graphite) and then treated thermally and thereafter converted into chips again.

The thorough mixing of the starting compounds can be effected in dry or in wet form.

If it is effected in dry form, the starting compounds are expediently used as finely divided powders and, after mixing and, if required, compaction, are subjected to the calcination (thermal treatment).

However, the thorough mixing is preferably effected in wet form. Usually, the starting compounds are mixed with one another in the form of an aqueous solution (if necessary in the presence of a complexing agent, cf. for example DE-A 10145958) and/or suspension. Thereafter, the aqueous material is dried and then calcined. Expediently, the aqueous material is an aqueous solution or an aqueous suspension. The drying process is preferably carried out immediately after the preparation of the aqueous mixture (particularly in the case of an aqueous solution, cf. for example JP-A 7-315842) and by spray drying (the exit temperatures are as a rule from 100 to 150° C.; the spray drying can be carried out by the cocurrent or countercurrent method), which requires a particularly thorough dry mixture, especially when the aqueous material to be spray dried is an aqueous solution or suspension. However, it can also be dried by evaporation under reduced pressure, by freeze drying or by conventional evaporation.

Suitable sources for the elemental constituents when carrying out the preparation method described above for multimetal oxide materials comprising i-phase/k-phase solid solutions are all those which are capable of forming oxides and/or hydroxides on heating (if required in air). Of course, oxides and/or hydroxides of the elemental constituents can themselves be concomitantly used or exclusively used as such starting compounds, i.e. all starting compounds mentioned in the publication of the prior art considered are particularly suitable.

Sources of the element Mo which are suitable according to the invention are, for example, molybdenum oxides, such as molybdenum trioxide, molybdates, such as ammonium heptamolybdate tetrahydrate, and molybdenum halides, such as molybdenum chloride.

Suitable starting compounds to be concomitantly used according to the invention for the element V are, for example, vanadium oxysulfate hydrate, vanadyl acetylacetonate, vanadates, such as ammonium metavanadate, vanadium oxides, such as vanadium pentoxide ($V_2O_5$), vanadium halides, such as vanadium tetrachloride ($VCl_4$), and vanadium oxyhalides, such as $VOCl_3$. Vanadium starting compounds which may be concomitantly used are also those which contain the vanadium in oxidation state +4.

According to the invention, suitable sources of the element tellurium are tellurium oxides, such as tellurium dioxide, metallic tellurium, tellurium halides, such as $TeCl_2$, and telluric acids, such as orthotelluric acid $H_6TeO_6$.

Advantageous antimony starting compounds are antimony halides, such as $SbCl_3$, antimony oxides, such as antimony trioxide ($Sb_2O_3$), antimonic acids, such as $HSb(OH)_6$, and antimony oxide salts, such as antimony oxide sulfate $(SbO)_2SO_4$.

Niobium sources suitable according to the invention are, for example, niobium oxides, such as niobium pentoxide ($Nb_2O_5$), niobium oxyhalides, such as $NbOCl_3$, niobium halides, such as $NbCl_5$, and complex compounds of niobium and organic carboxylic acids and/or dicarboxylic acids, e.g. oxalates and alcoholates. The Nb-containing solutions used in EP-A 895 809 are of course also suitable as a niobium source.

Regarding all other possible elements (in particular Pb, Ni, Cu, Co, Bi and Pd), suitable starting compounds are in particular their halides, nitrates, formates, oxalates, acetates, carbonates and/or hydroxides. Suitable starting compounds are often also the oxo compounds thereof, e.g. tungstates or the acids derived therefrom. Frequently, ammonium salts are also used as starting compounds.

Furthermore, suitable starting compounds are also polyanions of the Anderson type, as described, for example, in Polyhedron 6, No. 2 (1987), 213–218. A further suitable literature source for polyanions of the Anderson type is Kinetics and Catalysis, 40, No. 3 (1999), 401 to 404.

Other polyanions suitable as starting compounds are, for example, those of the Dawson or Keggin type. Those starting compounds which are converted into their oxides at elevated temperatures either in the presence or in the absence of oxygen, possibly with liberation of gaseous compounds, are preferably used.

The i-phase/k-phase multimetal oxide materials in the form of solid solutions, which are obtainable in the manner described (pure i-phase multimetal oxides are obtained only accidentally by the procedure described) can then be converted into novel multimetal oxides (I) by suitable washing in the manner described.

An increased fraction of i phase (and in favorable cases substantially pure i phase) is established in the preparation of precursor multimetal oxides (which can be converted into the novel multimetal oxides (I) by the washing described) when its preparation is carried out by a hydrothermal method, as described, for example, in DE-A 10029338 and JP-A 2000-143244.

However, the preparation of novel multimetal oxide materials (I) can also be carried out by first producing a multimetal oxide material I' which differs from multimetal oxide material (I) only in that d is 0.

Such a multimetal oxide material I', which is preferably finely divided, can then be impregnated with solutions (e.g. aqueous solutions) of elements $M^3$ (e.g. by spraying), then dried (preferably at $\leq 100°$ C.) and then calcined as described for the precursor multimetal oxides (preferably in an inert gas stream) (here, prior decomposition in air is preferably dispensed with). The use of aqueous nitrate and/or halide solutions of elements $M^3$ and/or the use of aqueous solutions in which the elements $M^3$ are present in a form complexed with organic compounds (e.g. acetates or acetylacetonates) is particularly advantageous for this preparation variant.

The novel multimetal oxides (I) obtainable in the manner described can be used as such [for example in the form of a powder or after pelleting of the powder (frequently with addition of from 0.5 to 2% by weight of finely divided graphite) and subsequent conversion into chips] or in the form of moldings for the novel process. The catalyst bed may be a fixed bed, a moving bed or a fluidized bed.

The shaping to give moldings can be effected, for example, by application to a support, as described in DE-A 10118814 or PCT/EP/02/04073 or DE-A 10051419.

The supports to be used for the multimetal oxide materials (I) to be employed according to the invention are preferably chemically inert, i.e. they substantially do not participate in the partial catalytic gas-phase oxidation or ammoxidation of the hydrocarbon (e.g. propane and/or propene to acrylic acid), which is catalyzed by the multimetal oxide materials (I) to be used according to the invention.

According to the invention, particularly suitable materials for the support are alumina, silica, silicates, such as clay, kaolin, steatite (preferably having a low water-soluble alkali content), pumice, aluminum silicate and magnesium silicate, silicon carbide, zirconium dioxide and thorium dioxide.

The surface of the support may be either smooth or rough. Advantageously, the surface of the support is rough since increased surface roughness generally results in greater adhesion of the applied coat of active material.

The surface roughness $R_z$ of the support is frequently from 5 to 200 µm, often from 20 to 100 µm (determined according to DIN 4768, Sheet 1, using a Hommel Tester for DIN-ISO measured surface variables from Hommelwerke, Germany).

Furthermore, the support material may be porous or nonporous. The support material is expediently nonporous (total volume of the pores, based on the volume of the support is $\leq 1\%$ by volume).

The thickness of the active oxide material coat present on the novel coated catalysts is usually from 10 to 1 000 µm. However, it may also be from 50 to 700 µm, from 100 to 600 µm or from 150 to 400 µm. Possible coat thicknesses are also from 10 to 500 µm, from 100 to 500 µm or from 150 to 300 µm.

In principle, any desired geometries of the supports are suitable for the novel process. Their longest dimension is as a rule from 1 to 10 mm. However, spheres or cylinders, in particular hollow cylinders, are preferably used as supports. Advantageous diameters for support spheres are from 1.5 to 4 mm. If cylinders are used as supports, their length is preferably from 2 to 10 mm and their external diameter preferably from 4 to 10 mm. In the case of rings, the wall thickness is moreover usually from 1 to 4 mm. Annular supports suitable according to the invention may also have a length of from 3 to 6 mm, an external diameter of from 4 to 8 mm and a wall thickness of from 1 to 2 mm. However, an annular support may also have the dimensions 7 mm×3 mm×4 mm or 5 mm×3 mm×2 mm (external diameter× length×internal diameter).

The preparation of coated catalysts to be used according to the invention can be effected in the simplest manner by preforming oxide materials of the formula (I) which are to be used according to the invention, converting them into a finely divided form and finally applying them to the surface of the support with the aid of a liquid binder. For this purpose, the surface of the support is moistened in the simplest manner with the liquid binder and brought into contact with finely divided active oxide material of the formula (I) to give a layer of the active material adhering to the moistened surface. Finally, the coated support is dried. Of course, the process can be repeated periodically to achieve a greater layer thickness. In this case, the coated substrate becomes the new support, etc.

The fineness of the catalytically active oxide material of the formula (I) which is to be applied to the surface of the support is of course adapted to the desired coat thickness. For example, those active material powders of which at least 50% of the total number of powder particles pass through a sieve of mesh size from 1 to 20 µm and whose numerical fraction of particles having a longest dimension above 50 µm is less than 10% are suitable for the coat thickness range from 100 to 500 µm. As a rule, as a result of the preparation, the distribution of longest dimensions of the powder particles corresponds to a Gaussian distribution. Frequently, the particle size distribution is as follows:

ened in a controlled manner absorb the supplied active material powder which, owing to the rolling movement, is compacted on the outer surface of the support, which, for example, is cylindrical or spherical, to give a cohesive coat.

If required, the support thus provided with a base coat passes again through the spray nozzles in the course of the subsequent revolution, is moistened in a controlled manner in order to be able to take up a further layer of finely divided oxidic active material in the course of the further movement, etc. (intermediate drying is as a rule not necessary). Finely divided oxidic active material and liquid binder are as a rule fed in continuously and simultaneously.

The liquid binder can be removed after coating is complete, for example by the action of hot gases, such as $N_2$ or air. It is noteworthy that the coating process described results in completely satisfactory adhesion of the successive layers to one another as well as of the base coat to the surface of the support.

What is important for the coating procedure described above is that the moistening of the support surface to be coated is carried out in a controlled manner. In brief, this means that the support surface is expediently moistened in such a way that it has adsorbed liquid binder but no liquid phase as such is visible on the support surface. If the support surface is too moist, the finely divided catalytically active oxide material agglomerates to form separate agglomerates instead of being applied to the surface. Detailed information in this context can be found in DE-A 2909671 and in DE-A 10051419.

The abovementioned final removal of the liquid binder used can be carried out in a controlled manner, for example by evaporation and/or sublimation. In the simplest case, this can be effected by the action of hot gases at a corresponding temperature (frequently from 50 to 300° C., often 150° C.). However, it is also possible to effect only preliminary drying

| | D (µm) | | | | | | | | | | | | | |
|---|---|---|---|---|---|---|---|---|---|---|---|---|---|---|
| | 1 | 1.5 | 2 | 3 | 4 | 6 | 8 | 12 | 16 | 24 | 32 | 48 | 64 | 96 | 128 |
| x | 80.5 | 76.3 | 67.1 | 53.4 | 41.6 | 31.7 | 23 | 13.1 | 10.8 | 7.7 | 4 | 2.1 | 2 | 0 | 0 |
| y | 19.5 | 23.7 | 32.9 | 46.6 | 58.4 | 68.3 | 77 | 86.9 | 89.2 | 92.3 | 96 | 97.9 | 98 | 100 | 100 |

Here: D = diameter of the particle, x = percentage of particles whose diameter is ≧ D and y = percentage of particles whose diameter is < D.

For carrying out the coating process described on an industrial scale, it is advisable, for example, to use the basic procedure disclosed in DE-A 2909671 and that disclosed in DE-A 10051419, i.e. the supports to be coated are initially taken in a preferably inclined (the angle of inclination is as a rule ≧0° and ≦90°, in general ≧30° and ≦90°; the angle of inclination is the angle between the central axis of the rotating container and the horizontal) rotating container (e.g. rotating pan or coating drum). The rotating container can raise the supports, for example spherical or cylindrical ones, under two metering apparatuses arranged a specific distance apart. The first of the two metering apparatuses expediently corresponds to a nozzle (for example an atomizer nozzle operated with compressed air), by means of which the supports rolling in the rotating pan are sprayed with the liquid binder and moistened in a controlled manner. The second metering apparatus is present outside the atomization cone of the liquid binder sprayed in and serves for feeding the finely divided oxidic active material (e.g. via a vibrating channel or a powder screw). The spherical supports moistby the action of hot gases. The final drying can then be effected, for example, in a drying oven of any desired type (e.g. a belt dryer) or in a reactor. The acting temperature should not be above the calcination temperature used for the preparation of the oxidic active material. Of course, the drying may also be carried out exclusively in a drying oven.

Independently of the type and geometry of the support, the following may be used as binder for the coating process: water, monohydric alcohols, such as ethanol, methanol, propanol and butanol, polyhydric alcohols, such as ethylene glycol, 1,4-butanediol, 1,6-hexanediol or glycerol, monobasic or polybasic organic carboxylic acids, such as propionic acid, oxalic acid, malonic acid, glutaric acid or maleic acid, amino alcohols, such as ethanolamine or diethanolamine, and monofunctional or polyfunctional organic amides, such as formamide. Other advantageous binders are solutions consisting of from 20 to 90% by weight of water and from 10 to 80% by weight of an organic compound which is dissolved in water and whose boiling point or sublimation temperature at atmospheric pressure (1 atm) is >100° C., preferably >150° C. Advantageously, the organic compound is selected from the above list of possible organic binders. The organic fraction of abovementioned aqueous binder solutions is preferably from 10 to 50, particularly preferably from 20 to 30, % by weight. Other suitable organic components are monosaccharides and oligosaccharides, such as glucose, fructose, sucrose or lactose, and polyethylene oxides and polyacrylates.

The fact that the preparation of coated catalysts suitable according to the invention can be effected not only by application of the prepared, finely milled active oxide materials of the formula (I) to the moistened support surface is important.

Rather, instead of the active oxide material, a finely divided precursor material thereof can also be applied to the moistened support surface (using the same coating process and binder) and the calcination can be carried out after drying of the coated support (it is also possible for supports to be impregnated with a precursor solution, then dried and subsequently calcined). If required, the phases other than the i phase can finally be washed out.

A suitable finely divided precursor material of this type is, for example, the material which is obtainable by first producing a very thorough, preferably finely divided, dry mixture from the sources of the elemental constituents of the desired active oxide material of the formula (I) (for example by spray drying of an aqueous suspension or solution of the sources) and then subjecting this finely divided dry mixture (if required after pelleting with addition of from 0.5 to 2% by weight of finely divided graphite) to a thermal treatment at from 150 to 350° C., preferably from 250 to 350° C., under an oxidizing (oxygen-containing) atmosphere (e.g. under air) for a few hours and, if required, finally subjecting said dry mixture to milling.

After the coating of the supports with the precursor material, calcination is then effected, preferably under inert gas atmosphere (all other atmospheres are also suitable) at from 360 to 700° C. or from 400 to 650° C. or from 400 to 600° C.

Of course, the shaping of multimetal oxide materials (I) which can be used according to the invention can also be effected by extrusion and/or pelleting of both finely divided multimetal oxide material (I) and finely divided precursor material of a multimetal oxide material (I) (if required, washing out of the phases other than the i phase may be effected at the end).

Suitable geometries are spheres, solid cylinders and hollow cylinders (rings). The longest dimension of the abovementioned geometries is as a rule from 1 to 10 mm. In the case of cylinders, their length is preferably from 2 to 10 mm and their external diameter preferably from 4 to 10 mm. In the case of rings, the wall thickness is moreover usually from 1 to 4 mm. Annular unsupported catalysts suitable according to the invention may also have a length of from 3 to 6 mm, an external diameter of from 4 to 8 mm and a wall thickness of from 1 to 2 mm. However, unsupported catalyst rings may also have dimensions of 7 mm×3 mm×4 mm or of 5 mm×3 mm×2 mm (external diameter×length×internal diameter).

Suitable geometries of the multimetal oxide materials (I) to be used for the novel process are of course all those in DE-A 10101695.

As stated above, what is important according to the invention is that the multimetal oxide materials (I) to be used according to the invention have an X-ray diffraction pattern (in this document, always based on Cu—$K_\alpha$ radiation) which has reflections h, i and k whose peaks are at the diffraction angles (2θ) 22.2±0.4° (h), 27.3±0.4° (i) and 28.2±0.4° (k), reflection h being the one with the strongest intensity within the X-ray diffraction pattern and having an FWHH of not more than 0.5°, intensity $P_i$ of the reflection i and the intensity $P_k$ of the reflection k fulfilling the relationship $0.65 \leq R \leq 0.85$, where R is the intensity ratio defined by the formula $$R = P_i/(P_i + P_k)$$

and the FWHH of the reflection i and of the reflection k is in each case $\leq 1°$.

At the same time, the X-ray diffraction pattern should have no reflections with the peak position 2θ=50.0±0.3°.

As stated above, the definition of the intensity of a reflection in the X-ray diffraction pattern is based in this document on the definition stated in DE-A 19835247, and that stated in DE-A 10051419 and DE-A 10046672.

This means that if $A^1$ is the peak of a reflection 1 and, in the line of the X-ray diffraction pattern, when viewed along the intensity axis perpendicular to the 2θ axis, $B^1$ is the nearest pronounced minimum (minima having shoulders are not taken into account) to the left of the peak $A^1$ and, in a corresponding manner, $B^2$ is the nearest pronounced minimum to the right of the peak $A^1$ and $C^1$ is the point at which a straight line drawn from the peak $A^1$ perpendicular to the 2θ axis intersects a straight line connecting the points $B^1$ and $B^2$, then the intensity of the reflection 1 is the length of the straight line section $A^1C^1$ which extends from the peak $A^1$ to the point $C^1$. The expression minimum means a point at which the gradient of a tangent to the curve in a base region of the reflection 1 changes from a negative value to a positive value, or a point at which the gradient tends to zero, the coordinates of the 2θ axis and of the intensity axis being used for determining the gradient.

In this document, the FWHH is in a corresponding manner the length of the resulting intercept between the two points of intersection $H^1$ and $H^2$ if a line parallel to the 2θ axis is drawn in the middle of the intercept $A^1C^1$, where $H^1$ and $H^2$ are in each case the first point of intersection of this parallel line with the above-defined line of the X-ray diffraction pattern to the left and right of $A^1$.

Figure 6:
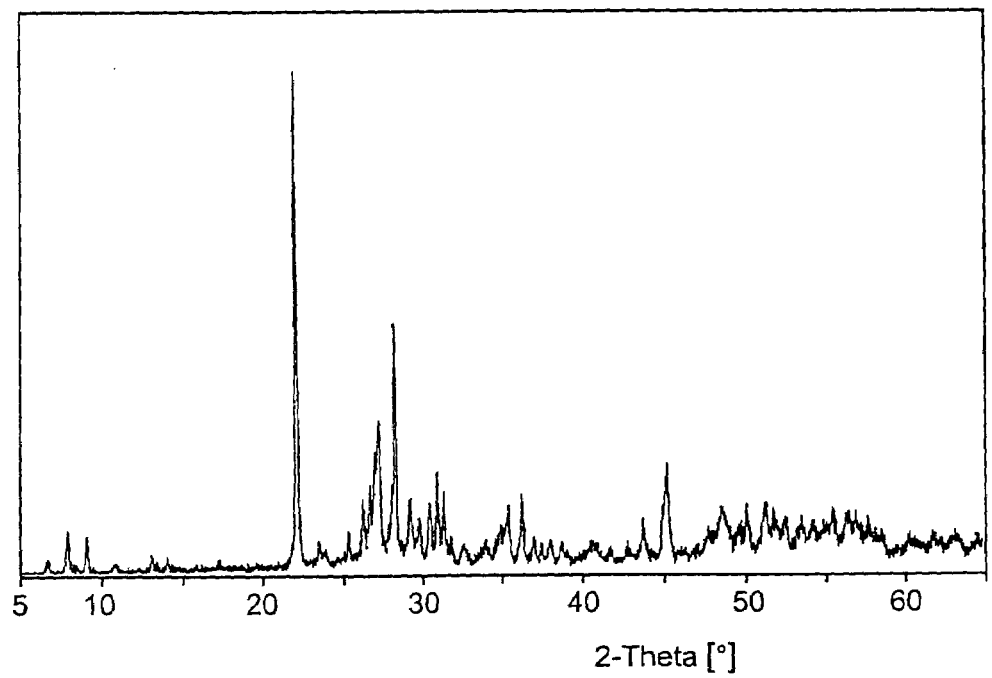
FIG. 6 shows the X-ray diffraction pattern of a material having the composition $Mo_{1.0}V_{0.33}Te_{0.22}Nb_{0.11}Pd_{0.004}O_x$.

An exemplary procedure for determining FWHH and intensity is also shown in FIG. 6 of DE-A 10046672.

The multimetal oxide materials (I) to be used according to the invention can of course also be used as a catalytic active material in a form diluted with finely divided, e.g. colloidal, materials, such as silica, titanium dioxide, alumina, zirconium oxide or niobium oxide.

The dilution mass ratio may be up to 9 (diluent):1 (active material), i.e. possible dilution mass ratios are, for example, 6 (diluent):1 (active material) and 3 (diluent):1 (active material). The diluent can be incorporated before and/or after the calcination, as a rule even before the drying.

If the incorporation is effected before the drying or before the calcination, the diluent must be chosen so that it is substantially preserved in the fluid medium or during the calcination. This is as a rule the case, for example, with oxides calcined at appropriately-high temperatures.

The novel multimetal oxide materials (I) are suitable, as such or in a form diluted as described above, as active materials for heterogeneously catalyzed partial gas-phase oxidations (including oxydehydrogenations) and/or ammoxidations of saturated and/or unsaturated hydrocarbons.

Such saturated and/or unsaturated hydrocarbons are in particular ethane, ethylene, propane, propylene, n-butane, isobutane and isobutene. Desired products are in particular acrolein, acrylic acid, methacrolein, methacrylic acid, acrylonitrile and methacrylonitrile. However, they are also suitable for the heterogeneously catalyzed partial gas-phase oxidation and/or ammoxidation of compounds such as acrolein and methacrolein.

However, ethylene, propylene and acetic acid may also be desired products.

In this document, the complete oxidation of the hydrocarbon is understood as meaning that all the carbon contained in the hydrocarbon is converted into oxides of carbon ($CO$, $CO_2$).

All reactions of the carbon, other than these, with reactive participation by molecular oxygen are subsumed in this document by the term partial oxidation. The additional reactive participation of ammonia denotes partial ammoxidation.

The novel multimetal oxide materials (I) recorded in this document are preferably suitable as catalytic active materials for the conversion of propane to acrolein and/or acrylic acid, of propane to acrylic acid and/or acrylonitrile, of propylene to acrolein and/or acrylic acid, of propylene to acrylonitrile, of isobutane to methacrolein and/or methacrylic acid, of isobutane to methacrylic acid and/or methacrylonitrile, of ethane to ethylene, of ethane to acetic acid and of ethylene to acetic acid.

The procedure for such partial oxidations and/or ammoxidations (by the choice of the content of ammonia in the reaction gas mixture, to be controlled in a manner known per se, the reaction can be designed substantially exclusively as a partial oxidation or exclusively as a partial ammoxidation or as a superposition of the two reactions; cf. for example WO 98/22421) is known per se from the i-phase/k-phase solid solutions of the prior art and can be carried out in a completely corresponding manner.

If the hydrocarbon used is crude propane or crude propylene, this preferably has the composition as described in DE-A 10246119 or DE-A 10118814 or PCT/EP/02/04073. The procedure, too, is preferably as described there.

A partial oxidation of propane to acrylic acid, to be carried out using catalysts comprising multimetal oxide (I) active material, can be effected, for example, as described in EP-A 608838, WO 0029106, JP-A 10-36311 and EP-A 1192987.

For example, air, air enriched with oxygen or air depleted in oxygen or pure oxygen can be used as a source of molecular oxygen required.

Such a process is also advantageous when the reaction gas starting mixture contains no noble gas, in particular no helium, as inert diluent gas. Otherwise, the reaction gas starting mixture can of course comprise inert diluent gases, e.g. $N_2$, $CO$ and $CO_2$, in addition to propane and molecular oxygen. Steam as a constituent of the reaction gas mixture is advantageous according to the invention.

This means that the reaction gas starting mixture with which the novel multimetal oxide active material is to be loaded at reaction temperatures of, for example, from 200 to 550° C. or from 230 to 480° C. or from 300 to 440° C. and pressures of from 1 to 10 bar or from 2 to 5 bar can have, for example, the following composition:

from 1 to 15, preferably from 1 to 7, % by volume of propane,
from 44 to 99% by volume of air and
from 0 to 55% by volume of steam.

Steam-containing reaction gas starting mixtures are preferred.

Suitable other possible compositions of the reaction gas starting mixture are:

from 70 to 95% by volume of propane,
from 5 to 30% by volume of molecular oxygen and
from 0 to 25% by volume of steam.

In such a process, a product gas mixture which does not consist exclusively of acrylic acid is of course obtained. Rather, in addition to unconverted propane, the product gas mixture contains byproducts, such as propene, acrolein, $CO_2$, $CO$, $H_2O$, acetic acid, propionic acid, etc., from which the acrylic acid has to be isolated.

This can be effected in the manner known for the heterogeneously catalyzed gas-phase oxidation of propene to acrylic acid.

This means that the acrylic acid present can be taken up from the product gas mixture by absorption with water or by absorption with a high-boiling inert hydrophobic organic solvent (for example a mixture of diphenyl ether and diphyl, which, if required, may also contain additives such as dimethyl phthalate). The resulting mixture of absorbent and acrylic acid can then be worked up by rectification, extraction and/or crystallization in a manner known per se to give pure acrylic acid. Alternatively, the basic isolation of the acrylic acid from the product gas mixture can also be effected by fractional condensation, as described, for example, in DE-A 19 924 532.

The resulting aqueous acrylic acid condensate can then be further purified, for example, by fractional crystallization (for example, suspension crystallization and/or layer crystallization).

The residual gas mixture remaining in the basic isolation of the acrylic acid contains in particular unconverted propane, which is preferably recycled to the gas-phase oxidation. For this purpose, it can be partly or completely separated from the residual gas mixture, for example by fractional rectification under superatmospheric pressure, and then recycled to the gas-phase oxidation. However, it is more advantageous if the residual gas is brought into contact, in an extraction apparatus, with a hydrophobic organic solvent which is preferably capable of absorbing the propane (for example by passing said solvent through).

By subsequent desorption and/or stripping with air, the absorbed propane can be liberated again and can be recycled to the novel process. In this way, economical total propane conversions are achievable. As in other separation processes, propene formed as a byproduct is as a rule not separated, or not completely separated, from the propane and is circulated with it. This also applies in the case of other homologous saturated and olefinic hydrocarbons. In particular, it applies very generally to novel heterogeneously catalyzed partial oxidations and/or ammoxidations of saturated hydrocarbons.

An evident advantageous aspect is that the novel multimetal oxide materials are also capable of heterogeneously catalyzing the partial oxidation and/or ammoxidation of the homologous olefinic hydrocarbon to the same desired product.

Thus, the novel multimetal oxide materials (I) can be used as active materials to prepare acrylic acid by heterogeneously catalyzed partial gas-phase oxidation of propene with molecular oxygen, as described in DE-A 10118814 or PCT/EP/02/04073 or JP-A 7-53448.

This means that a single reaction zone A is sufficient for carrying out the novel process. Exclusively catalysts comprising multimetal oxide material (I) are present as catalytically active materials in this reaction zone.

This is unusual since the heterogeneously catalyzed gas-phase oxidation of propene to acrylic acid takes place very generally in two steps in successive time spans. In the first step, propene is usually substantially oxidized to acrolein and, in the second step, acrolein formed in the first step is usually oxidized to acrylic acid.

Conventional processes for the heterogeneously catalyzed gas-phase oxidation of propene to acrylic acid therefore usually employ a special catalyst type tailored to the oxidation step for each of the two abovementioned oxidation steps.

This means that the conventional processes for the heterogeneously catalyzed gas-phase oxidation of propene to acrylic acid operate with two reaction zones in contrast to the novel process.

In the novel process for partial oxidation of propene in the one reaction zone A, it is of course also possible for only one or more than one catalyst comprising multimetal oxide material (I) to be present. Of course, the catalysts to be used according to the invention may be diluted with inert material as recommended in this document, for example also as support material.

In the novel process for the partial oxidation of propene, only one heating medium temperature, or a heating medium temperature changing along the reaction zone A, may prevail along the one reaction zone A, said heating medium being intended for heating the reaction zone A. This temperature change may be incremental or decremental.

If the novel process for the partial oxidation of propene is carried out as a fixed-bed oxidation, the procedure is expediently effected in a tube-bundle reactor whose catalyst tubes are loaded with the catalyst. Usually, a liquid, as a rule a salt bath, is passed as a heating medium around the catalyst tubes.

A plurality of temperature zones along the reaction zone A can then be realized in a simple manner by passing more than one salt bath around the catalyst tubes, section by section along the catalyst tubes.

Considered over the reactor, the reaction gas mixture is passed in the catalyst tubes either cocurrent with or countercurrent to the salt bath. The salt bath itself can execute a pure parallel flow relative to the catalyst tubes. However, a transverse flow can of course also be superposed on said parallel flow. Overall, the salt bath may also execute a meandering flow around the catalyst tubes, which flow, considered only over the reactor, is cocurrent with or countercurrent to the reaction gas mixture.

In the novel process for the partial oxidation of propene, the reaction temperature may be from 200 to 500° C. along the entire reaction zone A. Usually, it is from 250 to 450° C. The reaction temperature is preferably from 330 to 420° C., particularly preferably from 350 to 400° C.

In the novel process for the partial oxidation of propene, the operating pressure may be either 1 bar, less than 1 bar or more than 1 bar. According to the invention, typical operating pressures are from 1.5 to 10, frequently from 1.5 to 5, bar.

The propene to be used for the novel process for the partial oxidation of propene does not have to meet any particularly high requirements with respect to its purity.

As stated above and as for all one-stage or two-stage processes for the heterogeneously catalyzed gas-phase oxidation of propene to acrolein and/or acrylic acid very generally, for example, propene (also referred to as crude propene) having the following two specifications can be used entirely without problems as propene for such a process:

| a) Polymer grade propylene: | |
|---|---|
| $\geq$99.6% by weight | Propene, |
| $\leq$0.4% by weight | Propane, |
| $\leq$300 ppm by weight | Ethane and/or methane, |
| $\leq$5 ppm by weight | $C_4$-Hydrocarbons, |
| $\leq$1 ppm by weight | Acetylene, |
| $\leq$7 ppm by weight | Ethylene, |
| $\leq$5 ppm by weight | Water, |
| $\leq$2 ppm by weight | $O_2$, |
| $\leq$2 ppm by weight | Sulfur-containing compounds (calculated as sulfur), |
| $\leq$1 ppm by weight | Chlorine-containing compounds (calculated as chlorine), |
| $\leq$5 ppm by weight | $CO_2$, |
| $\leq$5 ppm by weight | CO, |
| $\leq$10 ppm by weight | Cyclopropane, |
| $\leq$5 ppm by weight | Propadiene and/or propyne, |
| $\leq$10 ppm by weight | $C_{\geq 5}$-Hydrocarbons and |
| $\leq$10 ppm by weight | Carbonyl-containing compounds (calculated as $Ni(CO)_4$). |

| b) Chemical grade propylene: | |
|---|---|
| $\geq$94% by weight | Propene, |
| $\leq$6% by weight | Propane, |
| $\leq$0.2% by weight | Methane and/or ethane, |
| $\leq$5 ppm by weight | Ethylene, |
| $\leq$1 ppm by weight | Acetylene, |
| $\leq$20 ppm by weight | Propadiene and/or propyne, |
| $\leq$100 ppm by weight | Cyclopropane, |
| $\leq$50 ppm by weight | Butene, |
| $\leq$50 ppm by weight | Butadiene, |
| $\leq$200 ppm by weight | $C_4$-Hydrocarbons, |
| $\leq$10 ppm by weight | $C_{\geq 5}$-Hydrocarbons, |
| $\leq$2 ppm by weight | Sulfur-containing compounds (calculated as sulfur), |
| $\leq$0.1 ppm by weight | Sulfides (calculated as $H_2S$), |
| $\leq$1 ppm by weight | Chlorine-containing compounds (calculated as chlorine), |
| $\leq$0.1 ppm by weight | Chlorides (calculated as $Cl^{\ominus}$) and |
| $\leq$30 ppm by weight | Water. |

Of course, all abovementioned possible impurities of propene can however also each be present in the crude propene in from two to ten times the stated individual amount without adversely affecting the usability of the crude propene for the novel process or for the known processes for the one-stage or two-stage heterogeneously catalyzed gas-phase oxidation of propene to acrolein and/or acrylic acid very generally.

This is true in particular when the saturated hydrocarbons, the steam, the oxides of carbon and the molecular oxygen are in any case compounds which participate in the reaction phenomenon either as inert diluent gas or as reactants in large amounts in the abovementioned processes. Usually, the crude propene as such is used as a mixture with recycle gas, air and/or molecular oxygen and/or dilute air and/or inert gas for the novel process and all other processes for the heterogeneously catalyzed gas-phase oxidation of propene to acrolein and/or acrylic acid.

Another suitable propene source for the novel process is propene which is formed as a byproduct in a process differing from the novel process and contains, for example, up to 40%, based on its weight, of propane. This propene may additionally be accompanied by other impurities which are substantially not troublesome in the novel process.

Both pure oxygen and air or air enriched with oxygen or depleted in oxygen may be used as an oxygen source for the novel process for the partial oxidation of propene.

In addition to molecular oxygen and propene, a reaction gas starting mixture to be used for the novel process usually also contains at least one diluent gas. Suitable diluent gases are nitrogen, oxides of carbon, noble gases and lower hydrocarbons, such as methane, ethane and propane (higher hydrocarbons, e.g. $C_4$ hydrocarbons, should be avoided). Frequently, steam is also used as a diluent gas. Mixtures of abovementioned gases frequently form a diluent gas for the novel process for the partial oxidation of propene.

According to the invention, the novel heterogeneously catalyzed oxidation of propene is effected advantageously in the presence of propane.

Typically, the reaction gas starting mixture for the novel process has the following composition (molar ratios):

Propene:oxygen:$H_2O$:other diluent gases=1:(0.1–10):(0–70):(0–20).

Preferably, the abovementioned ratio is 1:(1–5):(1–40):(0–10).

If the diluent gas used is propane, it can advantageously likewise be partly oxidized to acrylic acid in the novel process, as described.

According to the invention, the reaction gas starting mixture advantageously contains molecular nitrogen, CO, $CO_2$, steam and propane as diluent gas.

The molar ratio of propane to propene in the novel process may assume the following values: from 0 to 15, frequently from 0 to 10, often from 0 to 5, expediently from 0.01 to 3.

The propene space velocity of the catalyst load in the novel process for the partial oxidation of propene may be, for example, from 40 to 250 l(S.T.P.)/l vh. The space velocity of the reaction gas starting mixture is frequently from 500 to 15 000, in many cases from 600 to 10 000, often from 700 to 5 000, l(S.T.P.)/l Vh.

In the novel process for the partial oxidation of propene to acrylic acid, a product gas mixture which does not consist exclusively of acrylic acid is of course obtained. Rather, in addition to unconverted propene, the product gas mixture contains byproducts, such as propane, acrolein, $CO_2$, CO, $H_2O$, acetic acid, propionic acid, etc., from which the acrylic acid has to be isolated.

This can be effected as generally disclosed for the heterogeneously catalyzed two-stage gas-phase oxidation of propene to acrylic acid (carried out in two reaction zones).

This means that the acrylic acid present can be taken up from the product gas mixture by absorption with water or by absorption with a high-boiling inert hydrophobic organic solvent (for example, a mixture of diphenyl ether and diphyl which, if required, may also contain additives such as dimethyl phthalate). The resulting mixture of absorbent and acrylic acid can then be worked up by rectification, extraction and/or crystallization in a manner known per se to give pure acrylic acid. Alternatively, the basic isolation of the acrylic acid from the product gas mixture can also be effected by fractional condensation, as described, for example, in DE-A 19 924 532.

The resulting aqueous acrylic acid condensate can then be further purified, for example, by fractional crystallization (for example, suspension crystallization and/or layer crystallization).

The residual gas mixture remaining in the basic isolation of the acrylic acid contains in particular unconverted propene (and possibly propane). This can be separated from the residual gas mixture, for example, by fractional rectification under superatmospheric pressure and then recycled to the novel gas-phase oxidation. However, it is more advantageous to bring the residual gas into contact, in an extraction apparatus, with a hydrophobic organic solvent which is preferably capable of absorbing the propene (and any propane), for example by passing said solvent through.

By means of subsequent desorption and/or stripping with air, the absorbed propene (and any propane) can be liberated again and recycled to the novel process. In this way, economical total propene conversions are achievable. If propene is subjected to partial oxidation in the presence of propane, propene and propane are preferably separated off and recycled together.

In a completely corresponding manner, the novel multimetal oxides (I) can be used as catalysts for the partial oxidation of isobutane and/or isobutene to methacrylic acid.

Their use for the ammoxidation of propane and/or propene can be effected, for example, as described in EP-A 529853, DE-A 2351151, JP -A 6-166668 and JP-A 7-232071.

Their use for the ammoxidation of n-butane and/or n-butene can be effected as described in JP-A 6-211767.

Their use for the oxydehydrogenation of ethane to ethylene or the further reaction to acetic acid can be effected as described in U.S. Pat. No. 4250346 or as described in EP-B 261264.

The novel multimetal oxide materials (I) can, however, also be integrated into other multimetal oxide materials (for example, by mixing their finely divided materials, if required effecting compression and calcination, or mixing them in the form of sludges (preferably aqueous), and drying and calcining them (e.g. as described in EP-A 529853 for multimetal oxide materials (I) where d=0)). Once again, calcination is preferably effected under inert gas.

The resulting multimetal oxide materials (referred to below as overall materials) preferably contain $\geq 50$, particularly preferably $\geq 75$, very particularly preferably $\geq 90$ or 95, % by weight of multimetal oxide materials (I) and are likewise suitable for the partial oxidations and/or ammoxidations discussed in this document.

Furthermore, the overall materials preferably contain no reflection peak position at $2\Theta=50.0\pm0.3°$.

If the overall material contains a reflection peak position at $2\Theta=50.0\pm0.3°$, it is advantageous if the amount by weight of the novel multimetal oxide materials (I) is $\geq 80$ or $\geq 90$ or $\geq 95\%$ by weight. Such overall materials are obtainable, for example, by not effecting quantitative washout in the novel preparation process for the multimetal oxide materials (I).

The geometric shaping is expediently effected in the case of the overall materials as described for the multimetal oxide materials (I).

The advantageousness of the novel multimetal oxide materials (I) is based on their excellent selectivity with respect to desired product. It is surprising that the promoters $M^3$ are also effective in pure i phase, in particular with respect to both the partial oxidations and partial ammoxidations mentioned in the document.

For the purpose of the heterogeneously catalyzed partial gas-phase oxidation of propane to acrylic acid, the novel multimetal oxide materials (I) and multimetal oxide materials or catalysts containing them are preferably put into operation as described in DE-A 10122027.

EXAMPLES

A) Preparation of Coated Catalysts Comprising Multimetal Oxide Material

Comparative Example 1

Preparation of a Multimetal Oxide Catalyst Comprising the Active Material $Mo_{1.0}V_{0.33}Te_{0.19}Nb_{0.11}Ni_{0.01}O_x$, Containing i Phase and k Phase 87.61 g of ammonium metavanadate (78.55% by weight of $V_2O_5$, from G.f.E. Nürnbern, Germany) were dissolved at 80° C., with stirring, in 3 040 ml of water (three-necked flask with stirrer, thermometer, reflux condenser and heating). A clear, yellowish solution formed. This solution was cooled to 60° C. and then, while maintaining the 60° C., 117.03 g of telluric acid (99% by weight of $H_6TeO_6$, from Aldrich) and 400.00 g of ammonium heptamolybdate (82.52% by weight of $MoO_3$, from Starck/Goslar) were stirred into the solution in succession in the stated sequence. The resulting deep red solution was cooled to 30° C. and then, while maintaining the 30° C., 25.60 g of an aqueous solution of 6.80 g of nickel (II) nitrate hexahydrate (98% by weight, from Fluka) in 20 g of water (the solution was effected at 25° C.) were added. A solution A which was at 30° C. was thus obtained.

Separately from this, 112.67 g of ammonium niobium oxalate (20.8% by weight of Nb, from Starck/Goslar) were dissolved at 60° C. in 500 ml of water in a beaker to give a solution B. Solution B was cooled to 30° C. and combined at this temperature with solution A which was at the same temperature, with solution B being added to the solution A. The addition was effected steadily over a period of 5 minutes. An orange suspension formed.

This suspension was then spray-dried in a spray dryer from Niro (spray dryer Niro A/S Atomizer, Transportable Minor unit, central atomizer from Niro, DK). The temperature of the initially taken mixture was 30° C. The gas entry temperature $T^{in}$ was 320° C. and the gas exit temperature $T^{out}$ was 110° C. The resulting spray-dried powder was likewise orange.

100 g of the spray-dried powder were heated in a rotating-bulb furnace according to FIG. 1 (quartz glass bulb having an internal volume of 1 liter; 1=furnace housing, 2=rotating bulb, 3=heated space, 4=nitrogen/air stream) under an air stream of 50 l(S.T.P.)/h in the course of 27.5 minutes, initially linearly from 25° C. to 275° C., and this temperature and the air stream were then maintained for 1 hour. Immediately thereafter, the air stream was replaced by a nitrogen stream of 50 l(S.T.P.)/h and heating was carried out linearly from 275° C. to 600° C. in the course of 32.5 minutes. This temperature and the nitrogen stream were then maintained for 2 hours. Finally, the entire rotating bulb furnace was cooled to 25° C. while maintaining the nitrogen stream.

Figure 2:
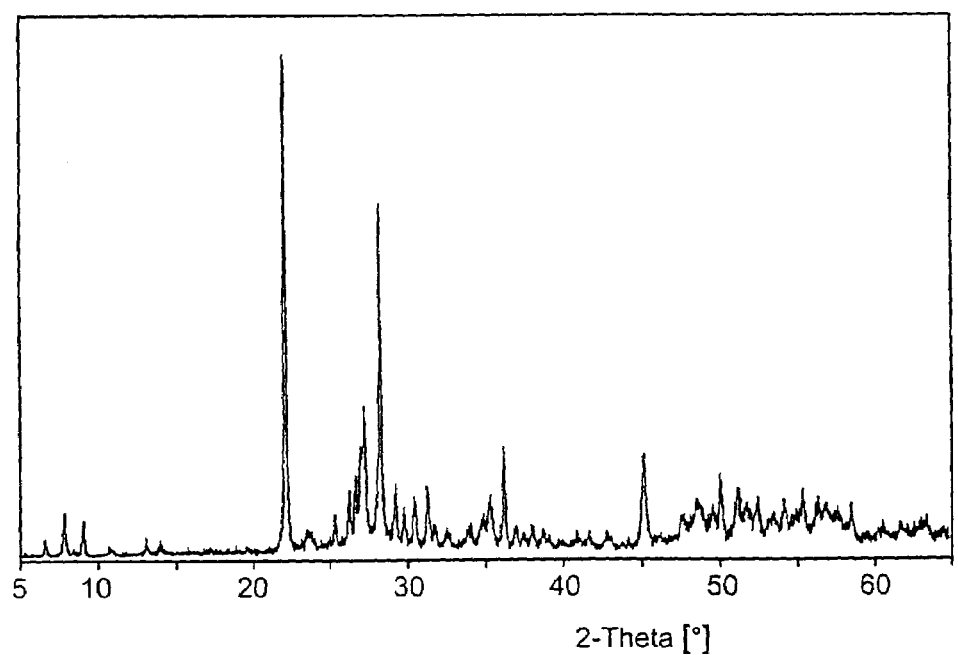
FIG. 2 shows an X-ray diffraction pattern for a black powder having the composition $Mo_{1.0}V_{0.33}Te_{0.19}Nb_{0.11}Ni_{0.01}O_x$.

A black powder having the composition $Mo_{1.0}V_{0.33}Te_{0.19}Nb_{0.11}Ni_{0.01}O_x$ (sample stoichiometry: $Mo_{1.0}V_{0.33}Te_{0.22}Nb_{0.11}Ni_{0.01}O_x$) was obtained. The associated X-ray diffraction pattern is shown in FIG. 2 (R=0.26). BET=8.0 m²/g.

The powder of the active material was then milled in a Retsch mill (centrifugal mill, type ZM 100, from Retsch, Germany) (particle size ≦0.12 mm).

38 g of the powder present after milling was applied to 150 g of spherical supports having a diameter of 2.2 to 3.2 mm ($R_z$=45 μm, support material=steatite from Ceramtec, Germany, total pore volume of the support ≦1% by volume, based on the total support volume). For this purpose, the support was initially taken in a coating drum having an internal volume of 2 l (angle of inclination of the central axis of the drum relative to the horizontal=30°). The drum was caused to rotate at 25 revolutions per minute. About 25 ml of a mixture of glycerol and water (glycerol:water weight ratio=1:3) was sprayed onto the support for 60 minutes via an atomizer nozzle operated with 300 l(S.T.P.)/h of compressed air. The nozzle was installed in such a way that the spray cone wet the supports conveyed to the uppermost point of the inclined drum by driver plates, in the upper half of the rolling zone. The finely divided powder of active material was introduced into the drum by means of a powder screw, the point of addition of the powder being within the rolling zone or below the spray cone. By periodic repetition of wetting and powder metering, the support provided with a base coat itself became the support in the subsequent period.

After completion of the coating, the coated support was dried under air for 16 hours at 150° C. in a muffle furnace. A coated catalyst CE1 comprising 20% by weight of active material resulted.

Example 1

Similar to comparative example 1. However, the powder resulting after the milling in the Retsch mill was stirred under reflux in 1 000 ml of a 10% strength by weight $HNO_3$ solution for 7 hours at 70° C. The remaining solid was filtered off from the resulting suspension and washed nitrate-free with water. The filter cake was then dried overnight with air at 110° C. in a muffle furnace.

Figure 3:
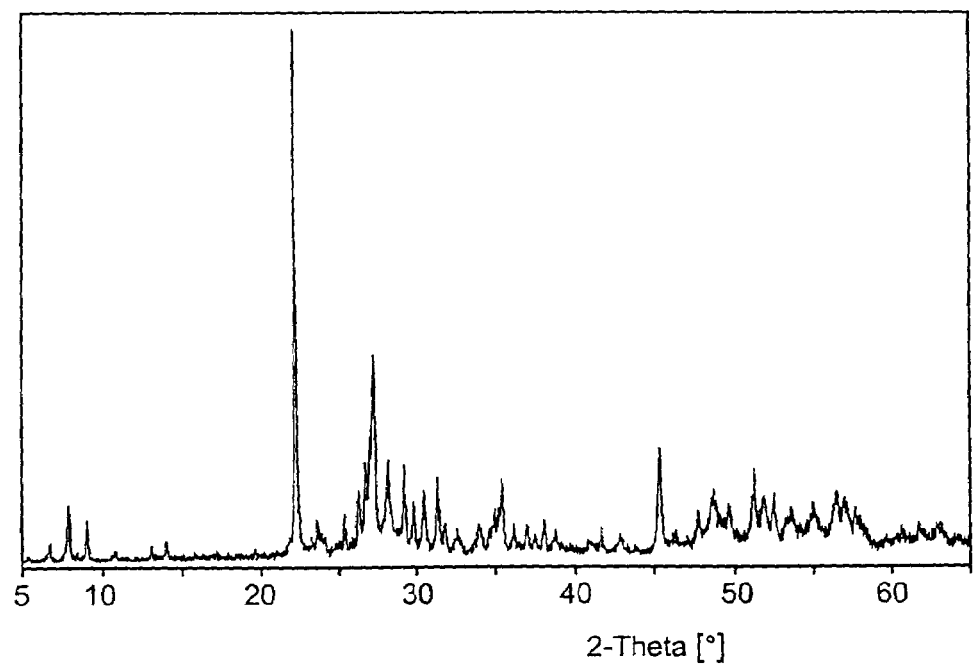
FIG. 3 shows the X-ray diffraction pattern for a material having the composition $Mo_{1.0}V_{0.29}Te_{0.14}Nb_{0.13}Ni_{0.007}O_x$.

The resulting active material had the composition $Mo_{0.1}V_{0.29}Te_{0.14}Nb_{0.13}Ni_{0.007}O_x$. The associated X-ray diffraction pattern is shown in FIG. 3 (R=0.71). BET=20.2 m²/g.

It was applied to the same support as in comparative example 1, in the same manner, so that a coated catalyst E1 comprising 20% by weight of active material resulted.

Comparative Example 2

Similar to comparative example 1, but 6.17 g of palladium (II) nitrate dihydrate (98%, Fluka) were used instead of 6.80 g of nickel(II) nitrate hexahydrate.

Figure 4:
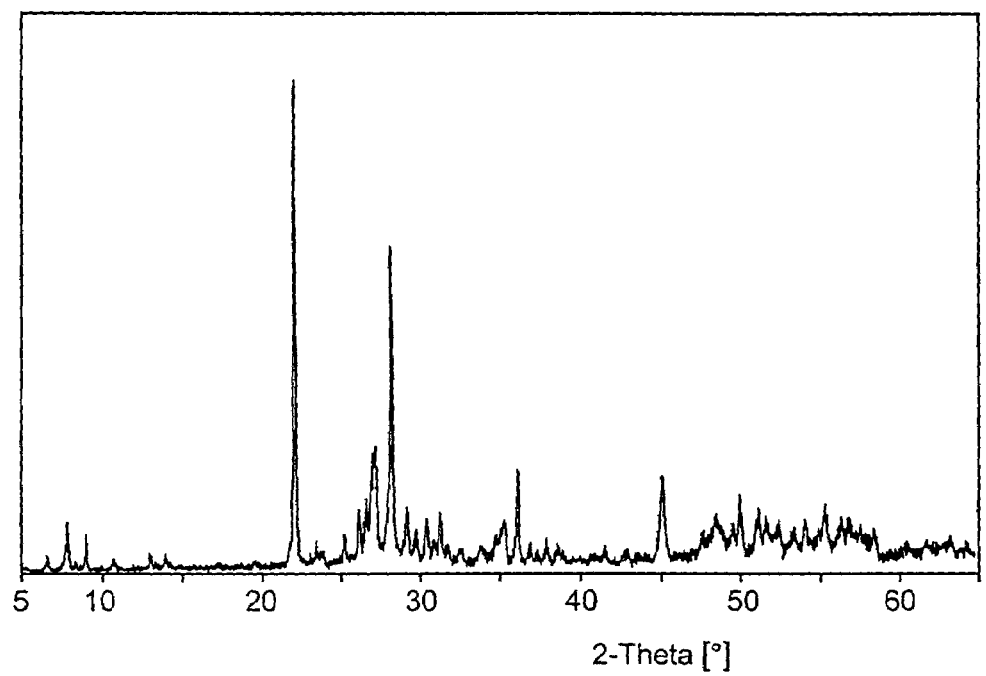
FIG. 4 shows the X-ray diffraction pattern for a material having the composition $Mo_{1.0}V_{0.33}Te_{0.19}Nb_{0.11}Pd_{0.01}O_x$.

The resulting active material had the composition $Mo_{1.0}V_{0.33}Te_{0.19}Nb_{0.11}Pd_{0.01}O_x$. The associated X-ray diffraction pattern is shown in FIG. 4 (R=0.25). BET=9.3 m²/g. It was applied to the same support as in comparative example 1, in the same manner, so that a coated catalyst CE2 comprising 20% by weight of active material resulted.

Example 2

Similar to example 1, but the active material from comparative example 2 was washed with aqueous nitric acid. The resulting active material had the composition $Mo_{1.0}V_{0.28}Te_{0.13}Nb_{0.13}Pd_{0.001}O_x$.

Figure 5:
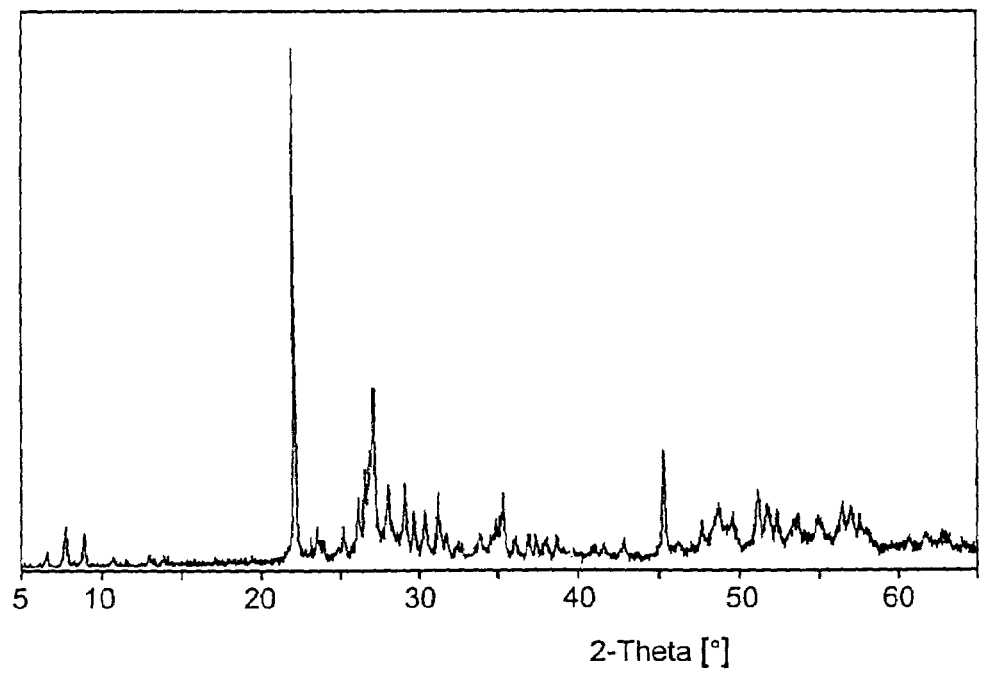
FIG. 5 shows the X-ray diffraction pattern of a material having the composition $Mo_{1.0}V_{0.28}Te_{0.13}Nb_{0.13}Pd_{0.001}O_x$.

The associated X-ray diffraction pattern is shown in FIG. 5 (R=0.73). BET=22.5 $m^2/g$. It was applied to the same substrate as in comparative example 1, in the same manner, so that a coated catalyst E2 comprising 20% by weight of active material resulted.

Comparative Example 3

Similar to comparative example 1, but the batch was halved in its amount and 12.34 g of palladium(II) nitrate dihydrate (98%, from Fluka) were used instead of 3.40 g of nickel(II) nitrate hexahydrate.

The resulting active material had the composition $Mo_{1.0}V_{0.33}Te_{0.22}Nb_{0.11}Pd_{0.04}O_x$. The associated X-ray diffraction pattern is shown in FIG. 6 (R=0.35). BET=9.3 $m^2/g$. It was applied to the same support as in comparative example 1, in the same manner, so that a coated catalyst CE3 comprising 20% by weight of active material resulted.

Example 3

Figure 7:
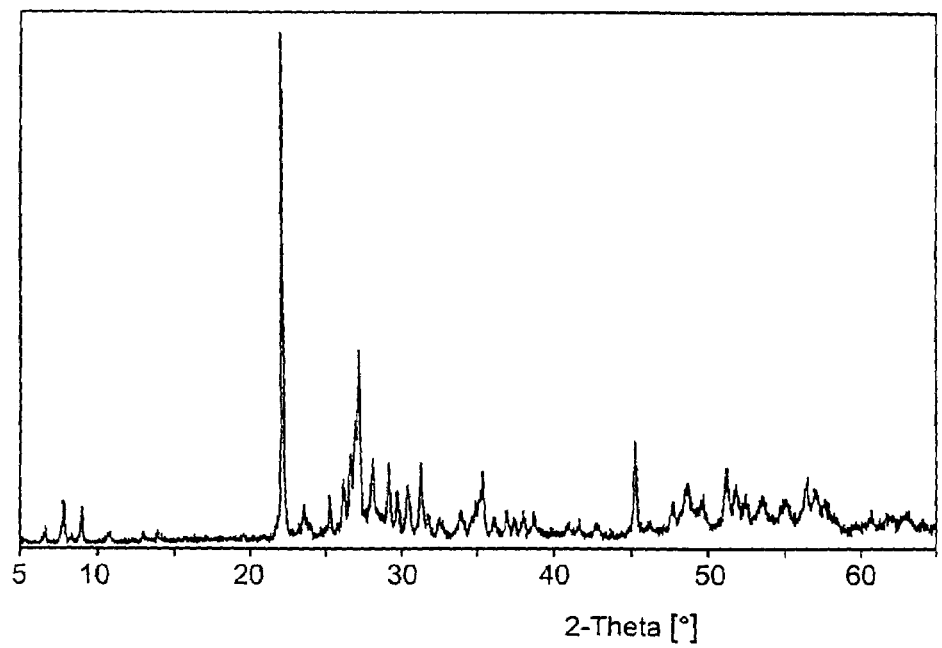
FIG. 7 shows the X-ray diffraction pattern of a material having the composition $Mo_{1.0}V_{0.29}Te_{0.13}Nb_{0.13}Pd_{0.001}O_x$.

Similar to example 1, but the active material from comparative example 3 was washed with aqueous nitric acid. The resulting active material had the composition $Mo_{1.0}V_{0.29}Te_{0.13}Nb_{0.13}Pd_{0.001}O_x$. The associated X-ray diffraction pattern is shown in FIG. 7 (R=0.74). BET=17.4 $m^2/g$. It was applied to the same support as in comparative example 1, in the same manner, so that a coated catalyst E2 comprising 20% by weight of active material resulted.

Comparative Example 4

Similar to comparative example 1, but 3.41 g of cobalt(II) nitrate hexahydrate (98%, from Riedel-de-Haen) were used instead of 6.80 g of nickel(II) nitrate hexahydrate.

Figure 8:
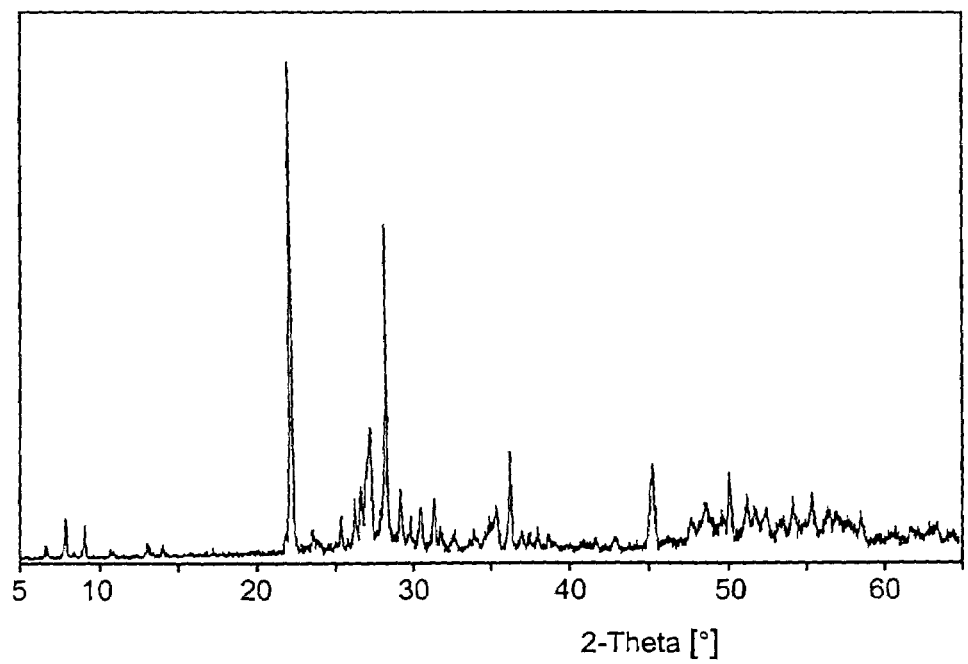
FIG. 8 shows the X-ray diffraction pattern of a material having the composition $Mo_{1.0}V_{0.33}Te_{0.19}Nb_{0.11}Co_{0.005}O_x$.

The resulting active material had the composition $Mo_{1.0}V_{0.33}Te_{0.19}Nb_{0.11}Co_{0.005}O_x$. The associated X-ray diffraction pattern is shown in FIG. 8 (R=0.24). BET=8.9 $m^2/g$. It was applied to the same support as in comparative example 1, in the same manner, so that a coated catalyst CE4 comprising 20% by weight of active material resulted.

Example 4

Figure 9:
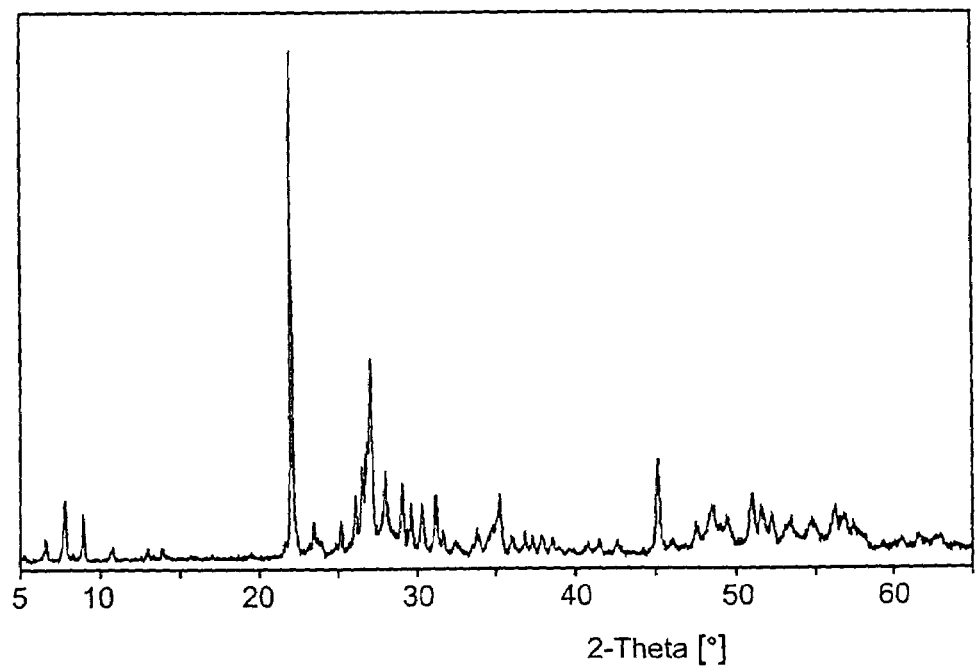
FIG. 9 shows the X-ray diffraction pattern of a material having the composition $Mo_{1.0}V_{0.29}Te_{0.13}Nb_{0.13}Co_{0.004}O_x$.

Similar to example 1, but the active material from comparative example 4 was washed with aqueous nitric acid. The resulting active material had the composition $Mo_{1.0}V_{0.29}Te_{0.13}Nb_{0.13}Co_{0.004}O_x$. The associated X-ray diffraction pattern is shown in FIG. 9 (R=0.73). BET=24.6 $m^2/g$. It was applied to the same support as in comparative example 1, in the same manner, so that a coated catalyst E4 comprising 20% by weight of active material resulted.

Comparative Example 5

Similar to comparative example 1, but 5.65 g of copper(II) nitrate trihydrate (99%, from Acros Organics) were used instead of 6.80 g of nickel(II) nitrate hexahydrate.

Figure 10:
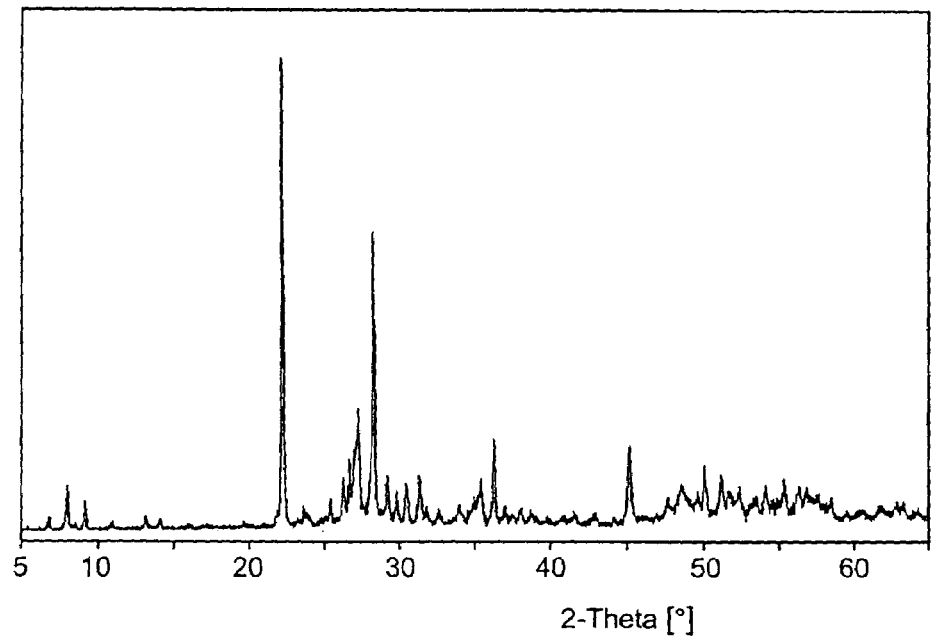
FIG. 10 shows the X-ray diffraction pattern of a material having the composition $Mo_{1.0}V_{0.33}Te_{0.19}Nb_{0.11}Cu_{0.01}O_x$.

The resulting active material had the composition $Mo_{1.0}V_{0.33}Te_{0.19}Nb_{0.11}Cu_{0.01}O_x$. The associated X-ray diffraction pattern is shown in FIG. 10 (R=0.27). BET=6.7 $m^2/g$. It was applied to the same support as in comparative example 1, in the same manner, so that a coated catalyst CE5 comprising 20% by weight of active material resulted.

Example 5

Similar to example 1, but the active material from comparative example 5 was washed with aqueous nitric acid.

Figure 11:
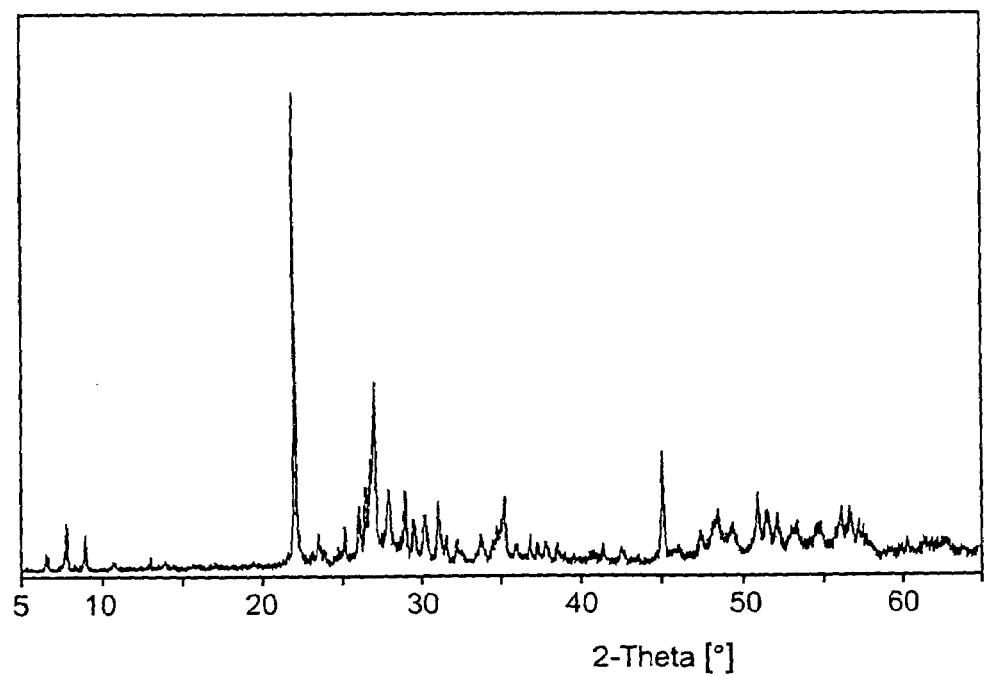
FIG. 11 shows the X-ray diffraction pattern of a material having the composition $Mo_{1.0}V_{0.28}Te_{0.13}Nb_{0.13}Cu_{0.003}O_x$.

The resulting active material had the composition $Mo_{1.0}V_{0.28}Te_{0.13}Nb_{0.13}Cu_{0.003}O_x$. The associated X-ray diffraction pattern is shown in FIG. 11 (R=0.74). BET=23.1 $m^2/g$. It was applied to the same support as in comparative example 1, in the same manner, so that a coated catalyst E5 comprising 20% by weight of active material resulted.

Comparative Example 6

Similar to comparative example 1, but 5.68 g of bismuth(III) nitrate pentahydrate (98.5%, from Merck) were used instead of 6.80 g of nickel(II) nitrate hexahydrate.

Figure 12:
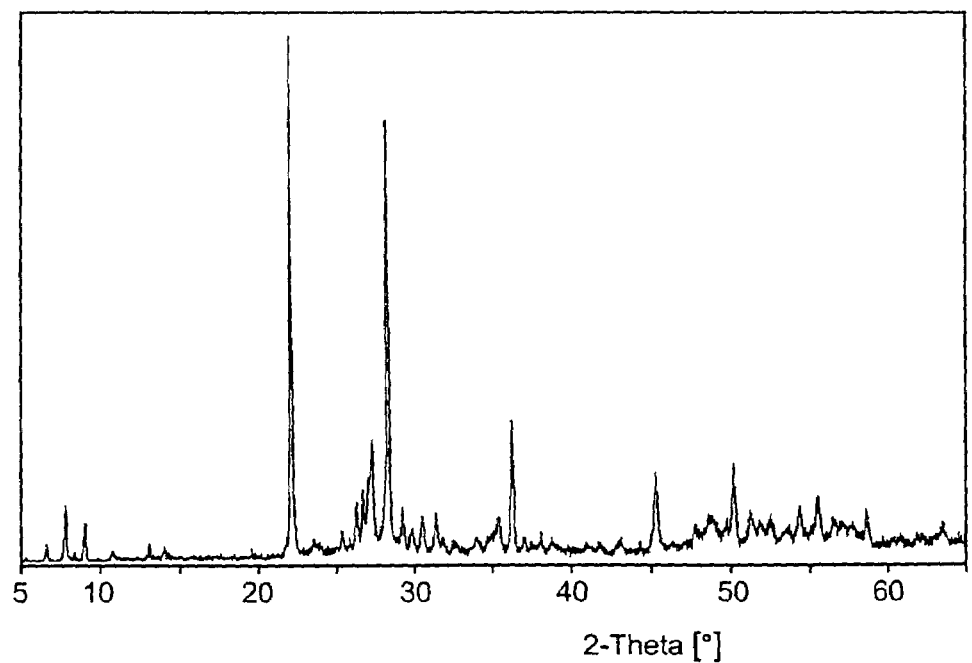
FIG. 12 shows the X-ray diffraction spectrum of a material having the composition $Mo_{1.0}V_{0.33}Te_{0.19}Nb_{0.11}Bi_{0.004}O_x$.

The resulting active material had the composition $Mo_{1.0}V_{0.33}Te_{0.19}Nb_{0.11}Bi_{0.004}O_x$. The associated X-ray diffraction pattern is shown in FIG. 12 (R=0.18). BET=9.0 $m^2/g$. It was applied to the same support as in comparative example 1, in the same manner, so that a coated catalyst CE6 comprising 20% by weight of active material resulted.

Example 6

Figure 13:
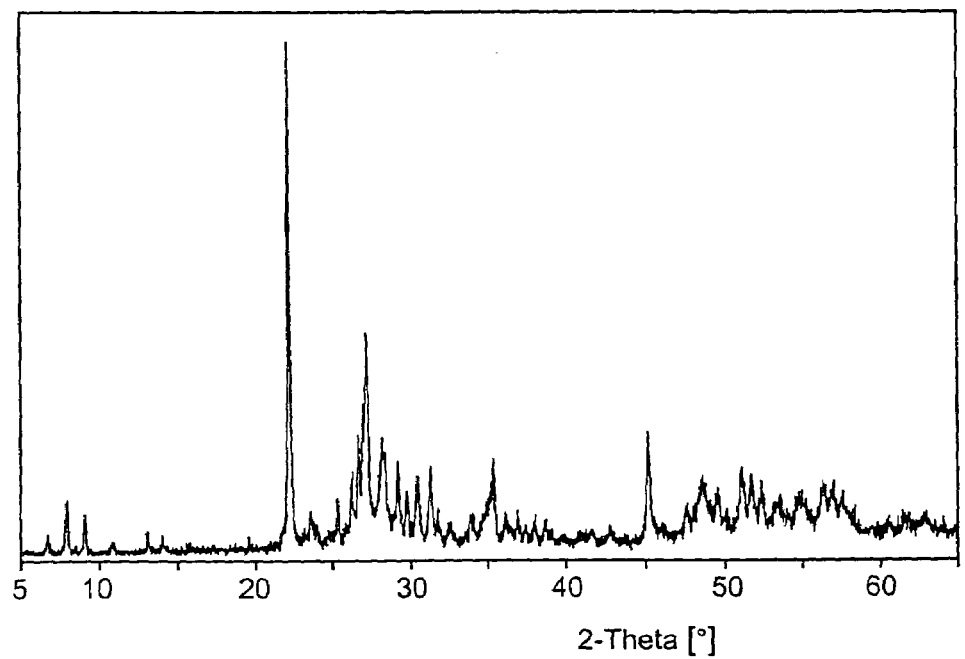
FIG. 13 shows the X-ray diffraction spectrum of a material having the composition $Mo_{1.0}V_{0.28}Te_{0.15}Nb_{0.14}Bi_{0.005}O_x$.

Similar to example 1, but the active material from comparative example 6 was washed with aqueous nitric acid. The resulting active material had the composition $Mo_{1.0}V_{0.28}Te_{0.15}Nb_{0.14}Bi_{0.005}O_x$. The associated X-ray diffraction pattern is shown in FIG. 13 (R=0.70). BET=22.0 $m^2/g$. It was applied to the same support as in comparative example 1, in the same manner, so that a coated catalyst E6 comprising 20% by weight of active material resulted.

Comparative Example 7

Similar to comparative example 1, but 3.84 g of lead(II) nitrate (Riedel-de-Haen, 99%) were used instead of 6.80 g of nickel(II) nitrate hexahydrate.

Figure 14:
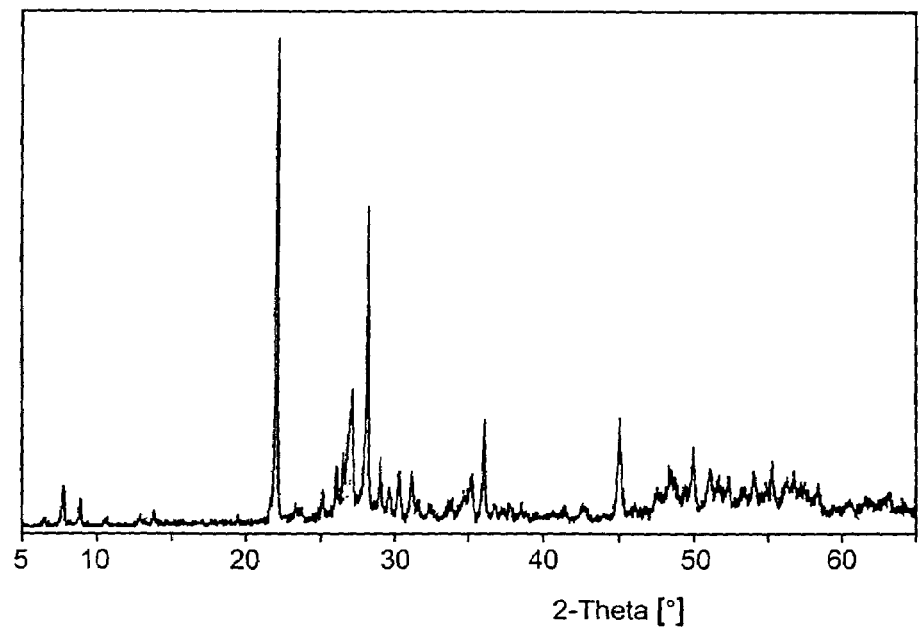
FIG. 14 shows the X-ray diffraction pattern of a material having the composition $Mo_{1.0}V_{0.34}Te_{0.18}Nb_{0.11}Pd_{0.004}$.

The resulting active material had the composition $Mo_{1.0}V_{0.34}Te_{0.18}Nb_{0.11}Pb_{0.004}$. The associated X-ray diffraction pattern is shown in FIG. 14 (R=0.30). BET=2.2 $m^2/g$. It was applied to the same support as in comparative example 1, in the same manner, so that a coated catalyst CE7 comprising 20% by weight of active material resulted.

Example 7

Similar to example 1, but the active material from comparative example 7 was washed with aqueous nitric acid. The resulting active material had the composition $Mo_{1.0}V_{0.28}Te_{0.13}Nb_{0.13}Pb_{0.001}O_x$.

Figure 15:
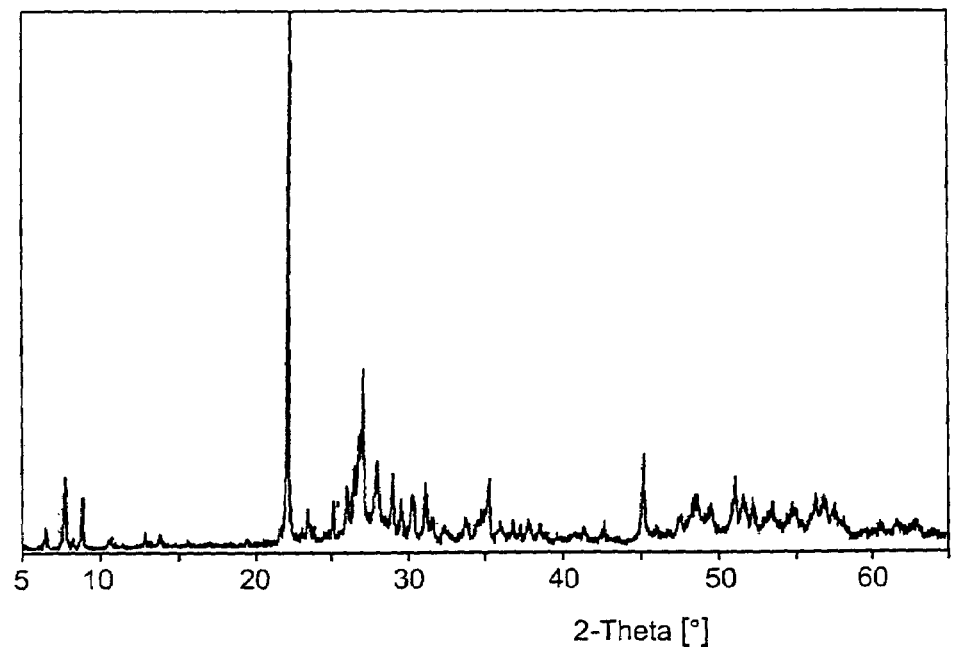
FIG. 15 shows the X-ray diffraction pattern of a material having the composition $Mo_{1.0}V_{0.28}Te_{0.13}Nb_{0.13}Pd_{0.001}O_x$.

The associated X-ray diffraction pattern is shown in FIG. 15 (R=0.67). BET=27.1 $m^2/g$. It was applied to the same support as in comparative example 1, in the same manner, so that a coated catalyst E7 comprising 20% by weight of active material resulted.

Comparative Example 8

Figure 16:
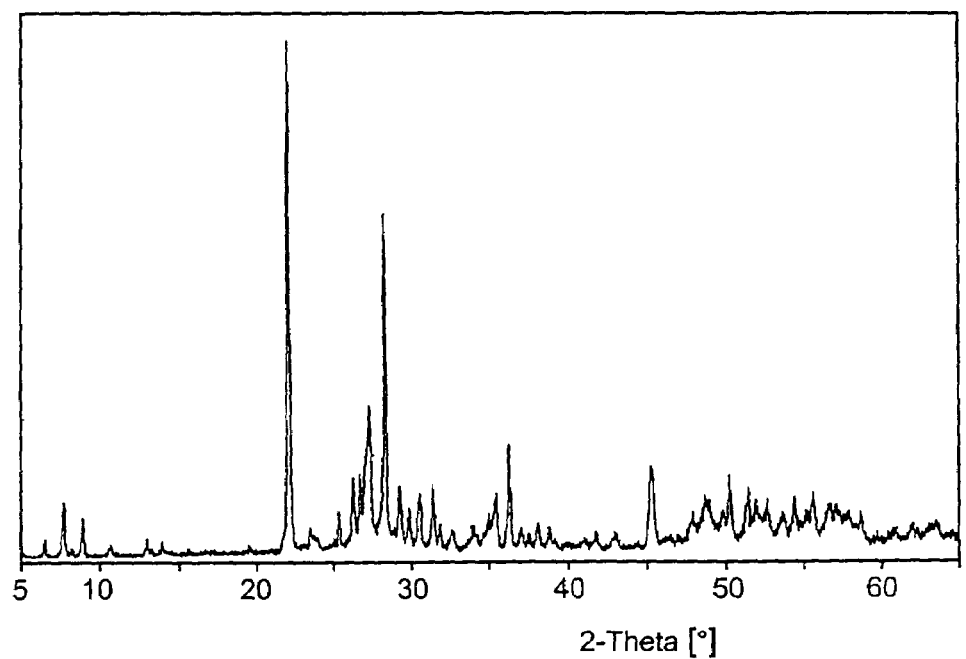
FIG. 16 shows the X-ray diffraction pattern of a material having the composition $Mo_{1.0}V_{0.33}Te_{0.16}Nb_{0.11}O_x$.

Similar to comparative example 1, but with the difference that the addition of 5.60 g of nickel(II) nitrate hexahydrate was not carried out. The resulting active material had the composition $Mo_{1.0}V_{0.33}Te_{0.16}Nb_{0.11}O_x$. The associated X-ray diffraction pattern is shown in FIG. 16 (R=0.26). BET=6.7 m²/g. It was applied to the same support as in comparative example 1, in the same manner, so that a coated catalyst CE7 comprising 20% by weight of active material resulted.

Comparative Example 9

Similar to example 1, but the active material from comparative example 7 was washed with aqueous nitric acid. The resulting active material had the composition $Mo_{1.0}V_{0.29}Te_{0.13}Nb_{0.13}O_x$.

Figure 17:
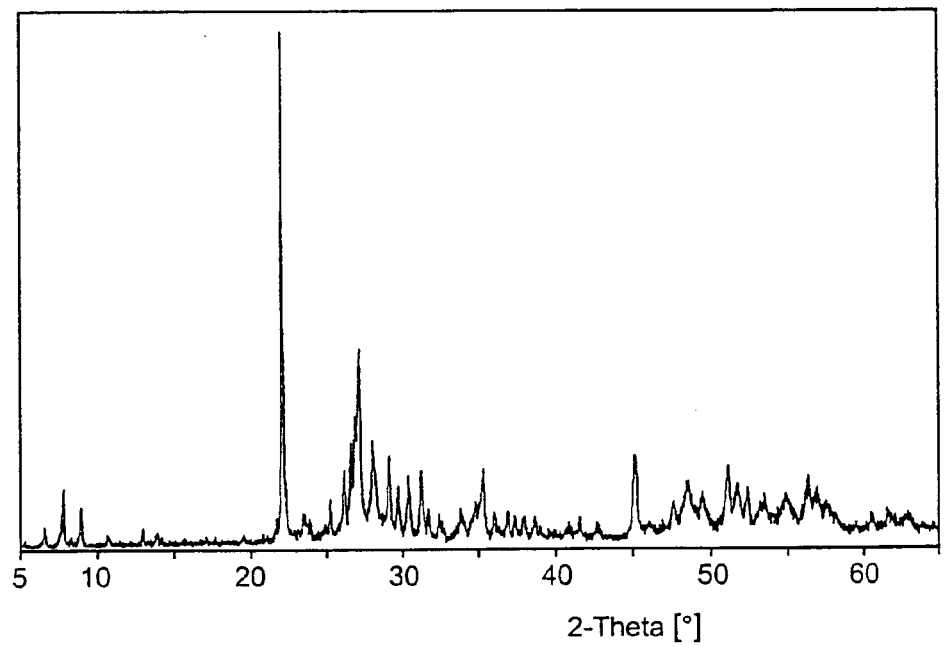
FIG. 17 shows the X-ray diffraction pattern of a material having the composition $Mo_{1.0}V_{0.29}Te_{0.13}Nb_{0.13}O_x$.

The associated X-ray diffraction pattern is shown in FIG. 17 (R=0.68). BET=26.0 m²/g. It was applied to the same support as in comparative example 1, in the same manner, so that a coated catalyst CE8 comprising 20% by weight of active material resulted.

B) Testing of the Coated Catalysts Prepared in A) and Comprising Multimetal Oxide Materials A tubular reactor (internal diameter: 8.5 mm, length: 140 cm, wall thickness: 2.5 cm) produced from steel was loaded with in each case 35.0 g of the respective coated catalyst from A) (catalyst bed length in all cases about 53 cm). A 30 cm upstream bed of steatite beads (diameter: from 2.2 to 3.2 mm, manufacturer: Ceramtec) was installed before the catalyst bed, and a downstream bed of the same steatite beads after the catalyst bed with the remaining length of the tubular reactor.

The external temperature of the loaded reaction tube was brought to 350° C. over the entire length from the outside by means of electrically heated heating mats.

The reaction tube was then fed with a reaction gas starting mixture having the molar composition of propane:air:$H_2O$=1:15:14 (the entry side was on the downstream bed side). The residence time (based on the catalyst bed volume) was brought to 2.4 seconds. The entry pressure was 2 bar absolute.

The reaction tube load was initially run in each case at the abovementioned external temperature of the loaded reaction tube over a period of 24 hours, before this external temperature was increased so that, based on a simple reaction tube pass, a propane conversion ($C_{PAN}$) of about 78 mol % resulted in all cases.

The table below shows the external temperature T (° C.) required for this conversion, as a function of the coated catalyst used, and the resulting selectivity of the acrylic acid formation ($S_{ACA}$ (mol %)) and the selectivity of the propene byproduct formation ($S_{PEN}$ (mol %)). In addition, the table shows the intensity ratio R of the active material present on the coated catalyst and the composition of this active material.

TABLE

| Example | Composition | R | T [° C.] | $C_{PAN}$ (mol %) | $S_{ACA}$ (mol %) | $S_{PEN}$ (mol %) |
|---|---|---|---|---|---|---|
| CE1 | $Mo_1V_{0.33}Te_{0.22}Nb_{0.11}Ni_{0.01}$ | 0.26 | 390 | 30 | 66 | 9 |
| E1 | $Mo_1V_{0.29}Te_{0.14}Nb_{0.11}Ni_{0.007}$ | 0.71 | 390 | 80 | 66 | 2 |
| CE2 | $Mo_1V_{0.33}Te_{0.19}Nb_{0.11}Pd_{0.01}$ | 0.25 | 390 | 80 | 62 | 1 |
| E2 | $Mo_1V_{0.28}Te_{0.13}Nb_{0.13}Pd_{0.001}$ | 0.73 | 420 | 77 | 59 | 1 |
| CE3 | $Mo_1V_{0.33}Te_{0.22}Nb_{0.11}Pd_{0.04}$ | 0.35 | 440 | 75 | 42 | 1 |
| E3 | $Mo_1V_{0.29}Te_{0.13}Nb_{0.13}Pd_{0.001}$ | 0.74 | 385 | 77 | 60 | 1 |
| CE4 | $Mo_1V_{0.33}Te_{0.19}Nb_{0.11}Co_{0.005}$ | 0.24 | 440 | 79 | 44 | 1 |
| E4 | $Mo_1V_{0.29}Te_{0.13}Nb_{0.13}Co_{0.004}$ | 0.73 | 390 | 76 | 62 | 2 |
| CE5 | $Mo_1V_{0.33}Te_{0.19}Nb_{0.11}Cu_{0.01}$ | 0.27 | 420 | 59 | 56 | 3 |

TABLE-continued

| Example | Composition | R | T [° C.] | $C_{PAN}$ (mol %) | $S_{ACA}$ (mol %) | $S_{PEN}$ (mol %) |
|---|---|---|---|---|---|---|
| E5 | $Mo_1V_{0.28}Te_{0.13}Nb_{0.13}Cu_{0.003}$ | 0.74 | 420 | 73 | 62 | 2 |
| CE6 | $Mo_1V_{0.33}Te_{0.19}Nb_{0.11}Bi_{0.004}$ | 0.18 | 400 | 83 | 54 | 1 |
| E6 | $Mo_1V_{0.28}Te_{0.15}Nb_{0.14}Bi_{0.005}$ | 0.70 | 410 | 77 | 62 | 1 |
| CE7 | $Mo_1V_{0.34}Te_{0.18}Nb_{0.11}Pb_{0.004}$ | 0.30 | 440 | 78 | 43 | 1 |
| E7 | $Mo_1V_{0.28}Te_{0.13}Nb_{0.13}Pb_{0.001}$ | 0.67 | 420 | 78 | 58 | 2 |
| CE8 | $Mo_1V_{0.33}Te_{0.16}Nb_{0.11}$ | 0.26 | 420 | 68 | 55 | 2 |
| CE9 | $Mo_1V_{0.29}Te_{0.13}Nb_{0.13}$ | 0.68 | 410 | 80 | 56 | 2 |

We claim:

1. A multimetal oxide material of the stoichiometry I

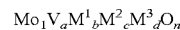

$$Mo_1V_aM^1_bM^2_cM^3_dO_n \qquad (I)$$

where
- $M^1$ is at least one of the elements selected from the group consisting of Te and Sb;
- $M^2$ is at least one of the elements selected from the group consisting of Nb, Ti, W, Ta and Ce;
- $M^3$ is at least one of the elements selected from the group consisting of pb, Ni, Co, Bi, Pd, Ag, Pt, Cu, Au, Ga, Zn, Sn, In, Re, Ir, Sm, Sc, Y, Pr, Nd and Tb;
- a is from 0.01 to 1;
- b is from >0 to 1,
- c is from >0 to 1,
- d is from >0 to 0.5 and
- n is a number which is determined by the valency and frequency of the elements other than oxygen in (I), whose X-ray diffraction pattern has reflections h, i and k whose peaks are at the diffraction angles (2Θ) 22.2±0.5° (h), 27.3±0.5° (i) and 28.2±0.5° (k), the reflection h being the one with the strongest intensity within the X-ray diffraction pattern and having an FWHH of not more than 0.5°, the intensity $P_i$ of the reflection i and the intensity $P_k$ of the reflection k fulfilling the relationship 0.65≦R≦0.85, where R is the intensity ratio defined by the formula $R=P_i/(P_i+P_k)$ and the FWHH of the reflection i and of the reflection k is in each case≦1°, wherein the at least one multimetal oxide material (I) is one whose X-ray diffraction pattern has no reflections with a peak i position 2Θ=50.0±0.3°.

2. The multimetal oxide material as claimed in claim 1, wherein 0.67≦R≦0.75.

3. The multimetal oxide material as claimed in claim 1, wherein 0.69≦R≦0.75.

4. The multimetal oxide material as claimed in claim 1, wherein 0.71≦R≦0.74.

5. The multimetal oxide material as claimed in claim 1, wherein R=0.72.

6. The multimetal oxide material as claimed in claim 1, wherein its specific surface area is from 11 to 40 m²/g.

7. The multimetal oxide material as claimed in claim 1, wherein its X-ray diffraction pattern also has further reflections with their peak positions at the following diffraction angles 2Θ:
- 9.0±0.4° (1),
- 6.7±0.4° (o) and
- 7.9±0.4° (p).

8. The multimetal oxide material as claimed in claim 7, wherein its X-ray diffraction pattern also has further reflections with their peak positions at the following diffraction angles $2\Theta$:
45.2±0.4° (q)
29.2±0.4° (m) and
35.4±0.4° (n).

9. The multimetal oxide material as claimed in claim 8, wherein, on the same intensity scale, the reflections h, i, l, m, n, o, p and q have the following intensities:
h=100,
i=from 5 to 95,
l=from 1 to 30,
m=from 1 to 40,
n=from 1 to 40,
o=from 1 to 30,
p=from 1 to 30 and
q=from 5 to 60.

10. The multimetal oxide material as claimed in claim 1, wherein a is from 0.05 to 0.6.

11. The multimetal oxide material as claimed in claim 1, wherein b is from 0.01 to 1.

12. The multimetal oxide material as claimed in claim 1, wherein c is from 0.01 to 1.

13. The multimetal oxide material as claimed in claim 1, wherein d is from 0.0005 to 0.5.

14. The multimetal oxide material as claimed in claim 1, wherein
a=is from 0.1 to 0.6;
b=is from 0.1 to 0.5;
c=is from 0.1 to 0.5 and
d=is from 0.001 to 0.5.

15. The multimetal oxide material as claimed in claim 1, wherein $M^2$ comprises at least 50 mol %, based on its total weight, of Nb.

16. The multimetal oxide material as claimed in claim 1, wherein $M^2$ comprises at least 75 mol %, based on its total weight, of Nb.

17. The multimetal oxide material as claimed in claim 1, wherein $M^2$ is exclusively Nb.

18. The multimetal oxide material as claimed in claim 1, wherein $M^3$ is at least one element from the group consisting of Ni, Co, Bi, Pd, Ag, Au, Pb and Ga.

19. The multimetal oxide material as claimed in claim 1, wherein $M^3$ is at least one element from the group consisting of Ni, Co, Pd and Bi.

20. The multimetal oxide material as claimed in claim 1, wherein $M^1$ is Te, $M^2$ is Nb and $M^3$ is at least one element selected from the group consisting of Ni, Co and Pd.

21. A multimetal oxide material which contains at least one multimetal oxide material as claimed in claim 1 and whose X-ray diffraction pattern has no reflection with the peak position $2\Theta=50.0\pm0.3°$.

22. The multimetal oxide material as claimed in claim 21, in which the multimetal oxide material (I) is present in a form diluted with at least one finely divided material from the group consisting of silica, titanium dioxide, alumina, zirconium oxide and niobium oxide.

23. A multimetal oxide material which comprises ≧80% by weight of at least one multimetal oxide material as claimed in claim 1 and whose X-ray diffraction pattern has a reflection with the peak position $2\Theta=50.0\pm0.3°$.

24. A process for the heterogeneously catalyzed partial gas-phase oxidation of at least one saturated or unsaturated hydrocarbon, wherein the catalytically active material used is at least one multimetal oxide material as claimed in claim 1.

25. The process as claimed in claim 24, wherein the hydrocarbon is propane, propene or a mixture of propane and propene.

26. A process for the heterogeneously catalyzed partial gas-phase ammoxidation of at least one saturated or unsaturated hydrocarbon, wherein the catalytically active material used is at least one multimetal oxide material as claimed in claim 1.

27. The process as claimed in claim 26, wherein the hydrocarbon is propane, propene or a mixture of propane and propene.

28. A method for partial oxidation and/or ammoxidation of at least one saturated and/or unsaturated hydrocarbon comprising utilizing at least one multimetal oxide material as claimed in claim 1 as a catalyst.

29. A process for the preparation of a multimetal oxide material as claimed in claim 1, wherein a thorough dry mixture is produced from sources of the elemental constituents of multimetal oxide material, said mixture is calcined at from 350 to 700° C. and the resulting product is washed with an aqueous solution of an organic and/or inorganic acid.

30. The multimetal oxide as claimed in claim 1, wherein d is from 0.003 to 0.5.

31. The multimetal oxide as claimed in claim 1, wherein d is from 0.004 to 0.5.

32. The multimetal oxide as claimed in claim 1, capable of converting 78 mol% or more of propane in a stream of propane, air in water in a ratio of 1:15:14 at a pressure of 2 bar absolute and a temperature of 350° C. to form acrylic acid with a selectivity of 58 mol% or greater.

33. The multimetal oxide as claimed in claim 1, capable of converting 73 mol% or more of propane in a stream of propane, air in water in a ratio of 1:15:14 at a pressure of 2 bar absolute and a temperature of 350° C. to form acrylic acid with a selectivity of 58 mol% or greater.

* * * * *